(12) United States Patent
Katsuda et al.

(10) Patent No.: US 9,895,205 B2
(45) Date of Patent: Feb. 20, 2018

(54) DENTAL TREATING APPARATUS AND DRIVING METHOD FOR THE SAME

(71) Applicant: J. Morita Manufacturing Corporation, Kyoto (JP)

(72) Inventors: Naoki Katsuda, Kyoto (JP); Seiichiro Yamashita, Kyoto (JP); Tomoaki Ueda, Kyoto (JP); Hideo Hijikata, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 233 days.

(21) Appl. No.: 14/489,967

(22) Filed: Sep. 18, 2014

(65) Prior Publication Data

US 2015/0086937 A1  Mar. 26, 2015

(30) Foreign Application Priority Data

Sep. 20, 2013 (JP) .................................. 2013-195624
Apr. 25, 2014 (JP) .................................. 2014-091390

(51) Int. Cl.
*A61C 1/00* (2006.01)
*A61C 1/02* (2006.01)
(Continued)

(52) U.S. Cl.
CPC .............. *A61C 5/025* (2013.01); *A61C 1/186* (2013.01); *A61C 5/40* (2017.02); *A61C 5/42* (2017.02);
(Continued)

(58) Field of Classification Search
USPC ...................................................... 433/27, 98
See application file for complete search history.

(56) References Cited

U.S. PATENT DOCUMENTS 5,980,248 A    11/1999  Kusakabe et al.
2002/0064756 A1*  5/2002  Pagnini .................... A61C 5/02
                                                    433/102
(Continued)

FOREIGN PATENT DOCUMENTS

EP    2431004 A1    3/2012
JP    3264607 B2    3/2002
(Continued)

OTHER PUBLICATIONS

Office Action dated Feb. 17, 2015 in counterpart Japanese Application No. 2014-091390 (with translation) (10 pages).
(Continued)

*Primary Examiner* — Nicole F Johnson
*Assistant Examiner* — Nicole F. Lavert
(74) *Attorney, Agent, or Firm* — Osha Liang LLP

(57) ABSTRACT

A dental treating apparatus according to the present invention includes: a hand piece; a head unit; a driving unit; a control unit; a load specifying unit; and a load comparing unit. The hand piece drivably holds a cutting tool on the head unit. The driving unit drives the cutting tool in a normal rotation direction or in a reverse rotation direction. The load comparing unit compares a load detected and a reference load. During a normal rotation period until driving for rotating the cutting tool in the normal rotation direction by the driving unit satisfies a predetermined first condition, the control unit maintains a rotation direction of the cutting tool in the normal rotation direction, and when a result of comparison by the load comparing unit attains a predetermined result during the normal rotation period, the control unit controls the rotation direction to the reverse rotation direction.

26 Claims, 17 Drawing Sheets

(51) Int. Cl.
   *A61C 5/02*  (2006.01)
   *A61C 19/04* (2006.01)
   *A61C 1/18*  (2006.01)
   *A61C 5/40*  (2017.01)
   *A61C 5/42*  (2017.01)
   *A61C 5/44*  (2017.01)
   *A61C 5/48*  (2017.01)

(52) U.S. Cl.
   CPC .............. *A61C 5/44* (2017.02); *A61C 5/48* (2017.02); *A61C 19/041* (2013.01); *A61C 1/003* (2013.01); *A61C 1/0023* (2013.01)

(56) References Cited

U.S. PATENT DOCUMENTS

2002/0182564 A1* 12/2002 Katsuda ............... A61C 1/0015
                                                    433/98
2005/0042572 A1   2/2005  Katsuda et al.
2013/0224677 A1   8/2013  Yamashita et al.
2014/0322669 A1  10/2014  Kunisada

FOREIGN PATENT DOCUMENTS

| | | |
|---|---|---|
| JP | 2003-504113 A | 2/2003 |
| JP | 3615209 B2 | 2/2005 |
| JP | 2005-144194 A | 6/2005 |
| JP | 3676753 B2 | 7/2005 |
| JP | 2013-172840 A | 9/2013 |
| WO | 01/03601 A1 | 1/2001 |
| WO | 2010/066337 A1 | 6/2010 |
| WO | 2013/108602 A1 | 7/2013 |
| WO | 2013/152346 A1 | 10/2013 |

OTHER PUBLICATIONS

Extended European Search Report dated Feb. 18, 2015 in counterpart European Application No. 14003023.0 (10 pages).

* cited by examiner

DENTAL TREATING APPARATUS AND DRIVING METHOD FOR THE SAME

BACKGROUND OF THE INVENTION

Field of the Invention

The present invention relates to a dental treating apparatus with a hand piece, and more specifically to a dental treating apparatus that causes a cutting tool for cutting and enlarging an inner wall of a root canal of a tooth to be driven, and a driving method for the dental treating apparatus.

Description of the Background Art

In dental treatment, a root canal of a tooth is cut and enlarged for treatment in some cases. For this treatment, a dental treating apparatus having a cutting tool (referred to as "file or reamer") attached to a head unit of a hand piece is used and the cutting tool is driven to cut and enlarge the root canal of the tooth. Japanese Patent No. 3264607, Japanese Patent No. 3615209 and Japanese Patent No. 3676753 disclose various types of driving control in order to, for example, prevent breakage due to a load applied to the cutting tool when the dental treating apparatus causes the cutting tool to be driven to cut and enlarge the root canal of the tooth.

A dental treating apparatus disclosed in Japanese Patent No. 3264607 includes detecting means for detecting a load applied to a cutting tool, and control means for rotating a cutting tool driving motor in a reverse rotation direction when the detected load reaches a preset reference.

A dental treating apparatus disclosed in Japanese Patent No. 3615209 includes driving means for driving a cutting tool, load detecting means for detecting a load applied to the cutting tool, root canal length measuring means for measuring a root canal length by using the cutting tool, reference load setting means for arbitrarily presetting a reference load, and control means for controlling the driving means. When the load detected by the load detecting means exceeds the reference load, the control means executes control to perform any one of the operations of stopping driving of the cutting tool, reducing an amount of driving, reversing rotation, and repeating normal rotation and reverse rotation, such that the load applied to the cutting tool is reduced. Furthermore, based on a value of the root canal length measured by the root canal length measuring means, the control means controls the driving means such that the amount of driving the cutting tool becomes smaller as a distance from the cutting tool to a root apex becomes shorter.

A dental treating apparatus disclosed in Japanese Patent No. 3676753 includes driving means for driving a cutting tool, root canal length measuring means for measuring a root canal length, and control means for controlling the driving means such that the driving force of the cutting tool changes in accordance with a value of the root canal length measured by the root canal length measuring means. The control means includes number-of-rotations control means for controlling the number of rotations of the cutting tool. Based on the value of the root canal length measured by the root canal length measuring means, the number-of-rotations control means controls the driving means such that the number of rotations of the cutting tool becomes smaller as a distance from the cutting tool to a root apex becomes shorter.

In a dental treating apparatus disclosed in Japanese National Patent Publication No. 2003-504113, a cutting tool is rotated clockwise or counterclockwise by a desired first rotation angle, and then, is rotated by a second rotation angle in a direction opposite to the first rotation angle. In order to discharge a cut piece from a root canal, the cutting tool is driven such that the first rotation angle is larger than the second rotation angle.

However, the cutting tool for cutting and enlarging the root canal of the tooth cuts into the root canal wall and contributes to cutting of the tooth when rotated clockwise, for example, whereas the cutting tool does not cut into the root canal wall and does not contribute to cutting of the tooth when rotated counterclockwise. Therefore, in the dental treating apparatus disclosed in Japanese National Patent Publication No. 2003-504113, the cutting tool is rotated clockwise or counterclockwise by the desired first rotation angle, and then, is rotated by the second rotation angle in the direction opposite to the first rotation angle, and thus, the rotation that does not contribute to cutting of the tooth is inevitably included, which resulted in a decrease in tooth cutting efficiency.

In addition, in the dental treating apparatus disclosed in Japanese Patent No. 3264607, control is executed to detect the load applied to the cutting tool, and rotate the cutting tool in the reverse rotation direction when the detected load reaches the preset reference. Therefore, in the dental treating apparatus disclosed in Japanese Patent No. 3264607, breakage of the cutting tool due to the applied load can be prevented, while the tooth cannot be cut while the load applied to the cutting tool is at the reference, which resulted in a decrease in efficiency of the work for cutting and enlarging the root canal of the tooth.

SUMMARY OF THE INVENTION

The present invention provides a dental treating apparatus that can enhance the tooth cutting efficiency while preventing breakage of a cutting tool due to an applied load, and a driving method for the dental treating apparatus.

A dental treating apparatus according to the present invention includes: a hand piece; a driving unit; a control unit; a load specifying unit; and a load comparing unit. The hand piece drivably holds a cutting tool on a head unit. The driving unit drives the cutting tool so as to be rotatable in a normal rotation direction in which the cutting tool cuts an object to be cut and in a reverse rotation direction opposite to the normal rotation direction. The control unit controls a rotation direction of the cutting tool. The load specifying unit specifies a load applied to the cutting tool. The load comparing unit compares the load specified by the load specifying unit and a reference load. During a normal rotation period until a predetermined first condition is satisfied, the control unit maintains the rotation direction of the cutting tool in the normal rotation direction, and when a result of comparison by the load comparing unit attains a predetermined result during the normal rotation period, the control unit controls the rotation direction of the cutting tool to the reverse rotation direction.

When the result of comparison by the load comparing unit attains the predetermined result during the normal rotation period, the dental treating apparatus according to the present invention controls the rotation direction of the cutting tool to the reverse rotation direction. Therefore, the load applied to the cutting tool can be reduced and breakage of the cutting tool due to the load can be prevented. Moreover, during the normal rotation period until the predetermined first condition is satisfied, the dental treating apparatus according to the present invention maintains the rotation direction of the cutting tool in the normal rotation direction. Therefore, the tooth cutting efficiency can be enhanced as compared with the driving method in which the cutting tool is rotated in the reverse rotation direction when the detected load reaches the reference.

Furthermore, in the dental treating apparatus according to the present invention, the cutting tool is rotated in the normal rotation direction by at least a predetermined rotation angle, and thereafter, the rotation direction is switched based on the result of comparison between the load applied to the cutting tool and the reference load. Therefore, driving in the normal rotation direction for cutting the tooth can be reliably ensured and the efficiency of the work for cutting and enlarging the root canal of the tooth can be improved.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, embodiments of the present invention are described with reference to the drawings.

(First Embodiment)

A dental treating apparatus according to a first embodiment of the present invention is a root canal treating device including a root canal enlarging and root canal length measuring system into which a dental hand piece for treatment on a root canal is incorporated. The dental treating apparatus according to the present invention is, however, not limited to the root canal treating device, and can be applied to a dental treating apparatus with a similar configuration.

Figure 1:
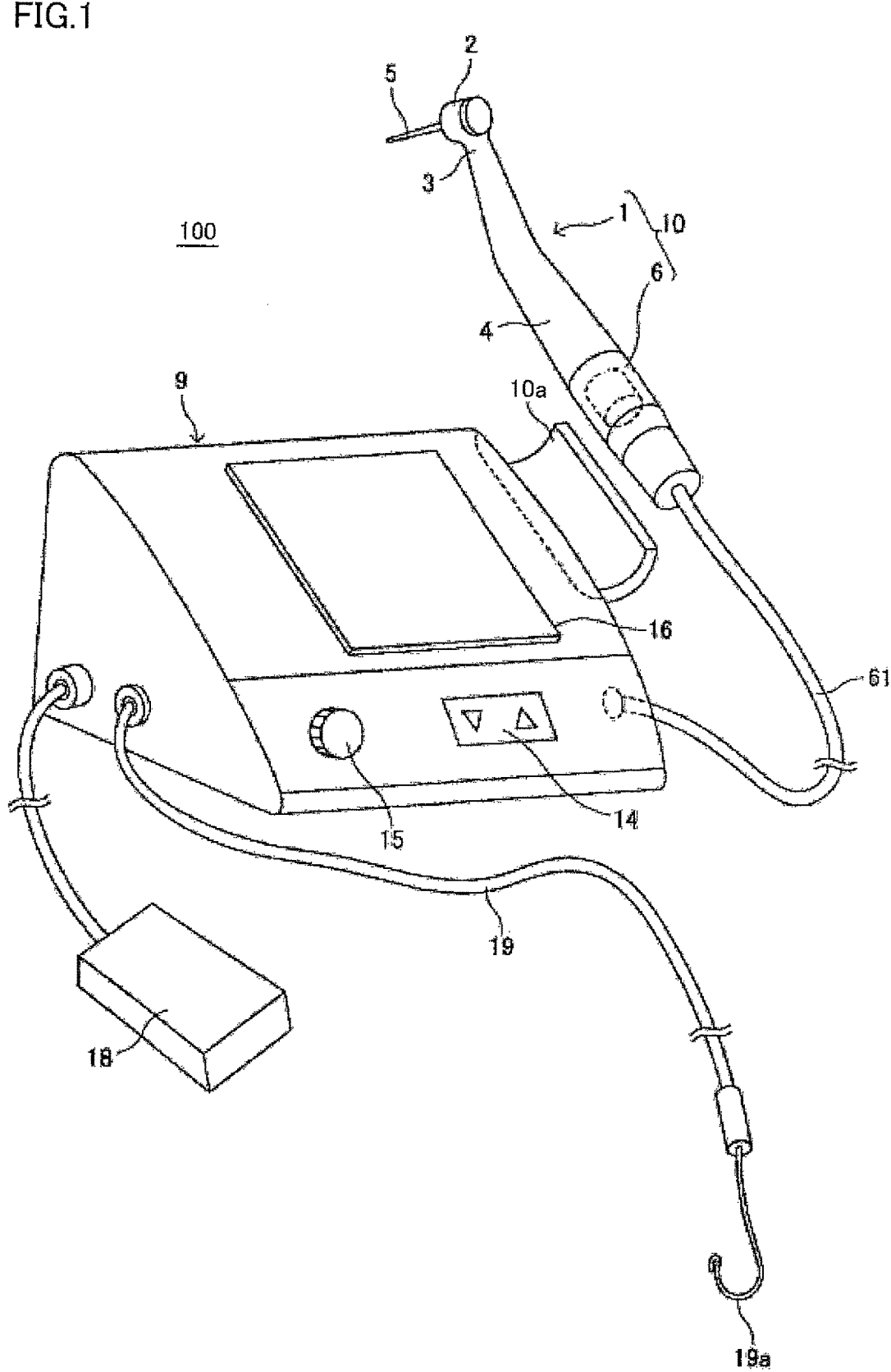
FIG. 1 is a schematic diagram showing an appearance of a configuration of a root canal treating device according to a first embodiment of the present invention.
Figure 2:
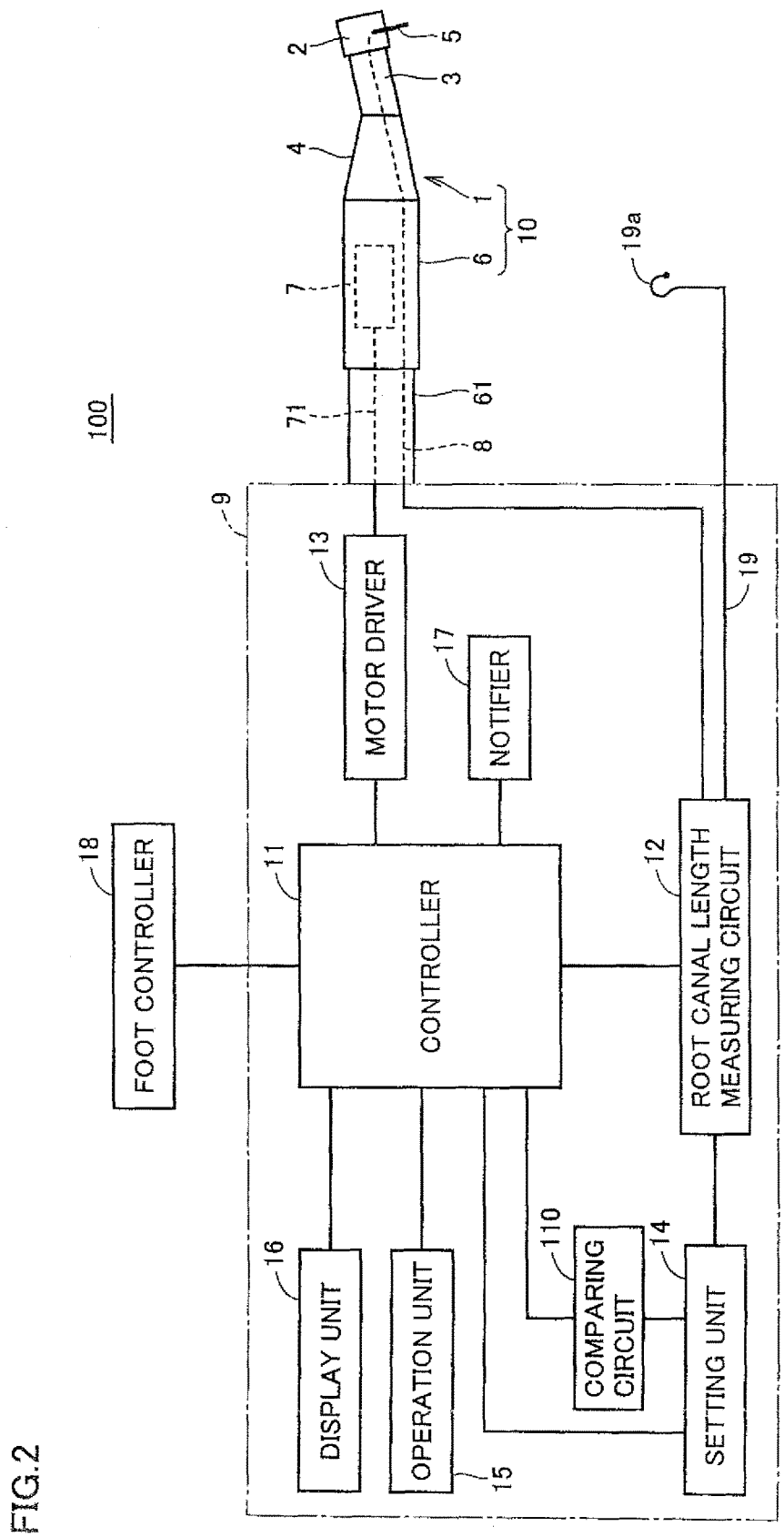
FIG. 2 is a block diagram showing a configuration of functions of the root canal treating device according to the first embodiment of the present invention.

FIG. 1 is a schematic diagram showing an appearance of a configuration of the root canal treating device according to the first embodiment of the present invention. FIG. 2 is a block diagram showing a configuration of functions of the root canal treating device according to the first embodiment of the present invention. A root canal treating device 100 as shown in FIG. 1 includes a hand piece 1 for treating dental root canal, a motor unit 6 and a control box 9.

Hand piece 1 for treating the dental root canal includes a head unit 2, a neck unit 3 with a small diameter connected to head unit 2, and a grip 4 connected to neck unit 3 and gripped by a hand or fingers. Further, to a base unit of grip 4, motor unit 6 is detachably connected for rotating and driving a cutting tool 5 (such as a file or a reamer) to be held on head unit 2. A dental instrument 10 is configured with hand piece 1 and motor unit 6 coupled to each other.

As shown in FIG. 2, a micro motor 7 is embedded in motor unit 6 that is connected to control box 9 through a hose 61 containing therein a power supply lead 71 for supplying power to micro motor 7, a signal lead 8 for transmitting a signal to a root canal length measuring circuit 12 to be described below, and the like. Here, signal lead 8 is a part of a conductive body for transmitting an electric signal, signal lead 8 being electrically connected to cutting tool 5 through motor unit 6 and hand piece 1. It is also noted that cutting tool 5 is one of electrodes of root canal length measuring circuit 12.

Control box 9 includes a controller 11, a comparing circuit 110, root canal length measuring circuit 12, a motor driver 13, a setting unit 14, an operation unit 15, a display unit 16, a notifier 17, and the like. As shown in FIG. 1, it should be noted that control box 9 is provided with a holder 10a holding instrument 10 when instrument 10 is not used, at a lateral part of a body. Also, a foot controller 18 is connected to controller 11 in control box 9. Further, a lead 19 is connected to root canal length measuring circuit 12 in control box 9. Although lead 19 is drawn out from control box 9, lead 19 may be drawn out to be bifurcated at an intermediate portion of hose 61. A mouth electrode 19a hung on a lip of a patient is attached to a tip end of lead 19 in an electrically conductive state. It should be noted that mouth electrode 19a is the other one of the electrodes of root canal length measuring circuit 12.

A primary part of controller 11 for controlling the whole system for enlarging the root canal and measuring the root canal length is configured by a microcomputer. Comparing circuit 110, root canal length measuring circuit 12, motor driver 13, setting unit 14, operation unit 15, display unit 16, notifier 17, and foot controller 18 are connected to controller 11. Assuming that a rotation direction in which cutting tool 5 cuts an object to be cut is a normal rotation and a rotation direction opposite to the normal rotation is a reverse rotation, controller 11 can perform normal rotation driving in which control is executed to perform driving for rotating cutting tool 5 in the normal rotation direction, reverse rotation driving in which control is executed to perform driving for rotating cutting tool 5 in the reverse rotation direction, and twist driving in which control is executed to perform driving for rotating cutting tool 5 by repeating the normal rotation and the reverse rotation. Controller 11 can change parameters such as a rotation angle and a rotation angular speed (number of rotations) in the normal rotation as well as a rotation angle and a rotation angular speed in the reverse rotation, and control driving for rotating cutting tool 5.

The rotation angular speed herein refers to an amount indicating the speed of rotation of cutting tool 5, and by dividing the rotation angular speed by $2\pi$ radian, the number of rotations is obtained. In the following embodiments, the speed of rotation of cutting tool 5 is indicated by using the number of rotations, instead of using the rotation angular speed. Revolutions per minute (rpm) is used as a unit of the number of rotations.

At any point in time until the driving for rotating cutting tool 5 in the normal rotation direction by motor driver 13 satisfies a predetermined condition (first condition) (during a normal rotation period), comparing circuit 110 performs load comparison. The first condition herein refers to a condition which is set based on various parameters described below such as a rotation angle and a driving period (rotation time) and which defines a timing for switching driving to the reverse rotation direction. Similarly, a second condition described below refers to a condition which is set based on various parameters described below such as a rotation angle and a driving period (rotation time) and which defines a timing for further switching driving to the reverse rotation direction.

Each time the driving for rotating cutting tool 5 in the normal rotation direction by a predetermined rotation angle (hereinafter, also simply referred to as "predetermined rotation angle") is performed, comparing circuit 110 compares a load applied to cutting tool 5 and a reference load. Namely, in comparing circuit 110, an interval of comparing the load applied to cutting tool 5 and the reference load is set as every time cutting tool 5 is rotated in the normal rotation direction by the predetermined rotation angle. Assuming that the predetermined rotation angle is, for example, 180 degrees, comparing circuit 110 compares the load applied to cutting tool 5 and the reference load twice, each time cutting tool 5 makes one rotation. Although the interval of performing load comparison in comparing circuit 110 is set by the rotation angle, the present invention is not limited thereto. The interval may be set by the driving period (rotation time) and the like. If the number of rotations of cutting tool 5 is fixed, setting the interval by the driving period means the same thing as setting the interval by the rotation angle. When the number of rotations of cutting tool 5 is, for example, 120 rpm, rotating cutting tool 5 by 180 degrees means the same thing as driving cutting tool 5 for 0.25 seconds. Furthermore, the interval of performing load comparison in comparing circuit 110 is not limited to until the driving for rotating cutting tool 5 in the normal rotation direction by motor driver 13 satisfies the predetermined rotation angle or the driving period (rotation time). For example, the interval of performing load comparison in comparing circuit 110 may be defined by an amount of current or a voltage value supplied from motor driver 13 to micro motor 7, or may be defined by a value of a control signal supplied to motor driver 13, and the like. The interval of performing load comparison in comparing circuit 110 may only be defined as until the driving for rotating cutting tool 5 in the normal rotation direction by motor driver 13 satisfies the predetermined condition (first condition).

Root canal length measuring circuit 12 configures a closed circuit with cutting tool 5 inserted in the root canal of the tooth as one electrode and mouth electrode 19a hung on the lip of the patient as the other electrode. Root canal length measuring circuit 12 can measure a distance from an apical position of the tooth to a tip end of cutting tool 5 by applying voltage between cutting tool 5 and mouth electrode 19a and measuring impedance between cutting tool 5 and mouth electrode 19a. An amount of insertion of the cutting tool, that is, a distance from an opening of the root canal to the tip end of the cutting tool, when root canal length measuring circuit 12 detects that the tip end of cutting tool 5 has reached the apical position can be defined as the root canal length. It should be noted that a method for electrically measuring the root canal length by measuring the impedance between cutting tool 5 and mouth electrode 19a is publicly known and all publicly-known methods for electrically measuring the root canal length can be applied to root canal treating device 100 according to the first embodiment.

Motor driver 13 is connected to micro motor 7 via power supply lead 71 and controls the power supplied to micro motor 7 based on a control signal from controller 11. Motor driver 13 can control the rotation direction, the number of rotations, the rotation angle and the like of micro motor 7, namely the rotation direction, the number of rotations, the rotation angle and the like of cutting tool 5 by controlling the power supplied to micro motor 7.

Setting unit 14 sets a reference for controlling the rotation direction, the number of rotations, the rotation angle and the like of cutting tool 5. Setting unit 14 can also set the reference load compared with the load applied to cutting tool 5 in comparing circuit 110, and the rotation angle indicating the interval of comparison, and can set the apical position or a position located at a prescribed distance from the apical position as a reference position in advance by using root canal length measuring circuit 12. Since the reference position is set in setting unit 14 in advance, root canal treating device 100 can change the parameters such as the rotation direction, the number of rotations and the rotation angle of cutting tool 5 when the tip end of cutting tool 5 reaches this reference position.

In addition to setting the parameters such as the number of rotations and the rotation angle of cutting tool 5, operation unit 15 can also select whether to perform root canal length measurement or not. Operation unit 15 can also manually switch between the normal rotation driving and the reverse rotation driving as well as between the normal rotation driving and the twist driving.

Display unit 16 displays a position of the tip end of cutting tool 5 in the root canal and the rotation direction, the number of rotations, the rotation angle and the like of cutting tool 5 as described below. Also, display unit 16 can display information for notifier 17 to notify a user.

Notifier 17 notifies the user by light, sound, vibration, and the like of the driving state of cutting tool 5 that is being executed by controller 11. Specifically, notifier 17 includes an LED (Light Emitting Diode), a speaker, an oscillator, and the like according to the need to notify the user of the driving state of cutting tool 5, and colors of the light emitted from the LED change or sounds outputted from the speaker change based on whether the driving in the normal rotation direction is being executed or the driving in the reverse rotation direction is being executed. Also, notifier 17 need not include the LED, the speaker, the oscillator and the like separately if display unit 16 can display the driving state of cutting tool 5 for the user.

Foot controller 18 is an operation unit for performing driving control on cutting tool 5 by micro motor 7 by a stepping operation. It should be noted that the driving control on cutting tool 5 by micro motor 7 is not limited to foot controller 18, namely, an operation switch (not shown) is provided in grip 4 of hand piece 1 to perform the driving control on cutting tool 5 by this operation switch and foot controller 18. Also, for example, in a state where the stepping operation via foot controller 18 is performed, and further when root canal length measuring circuit 12 detects that cutting tool 5 has been inserted into the root canal, the rotation of cutting tool 5 may be started.

It should be noted that a configuration is disclosed in that control box 9 of root canal treating device 100 is put on a tray table or a side table installed on a lateral part of a dental treatment table and used. The present invention is, however, not limited to such a configuration but can include a configuration in that control box 9 is incorporated into the tray table or the side table.

Figure 3:
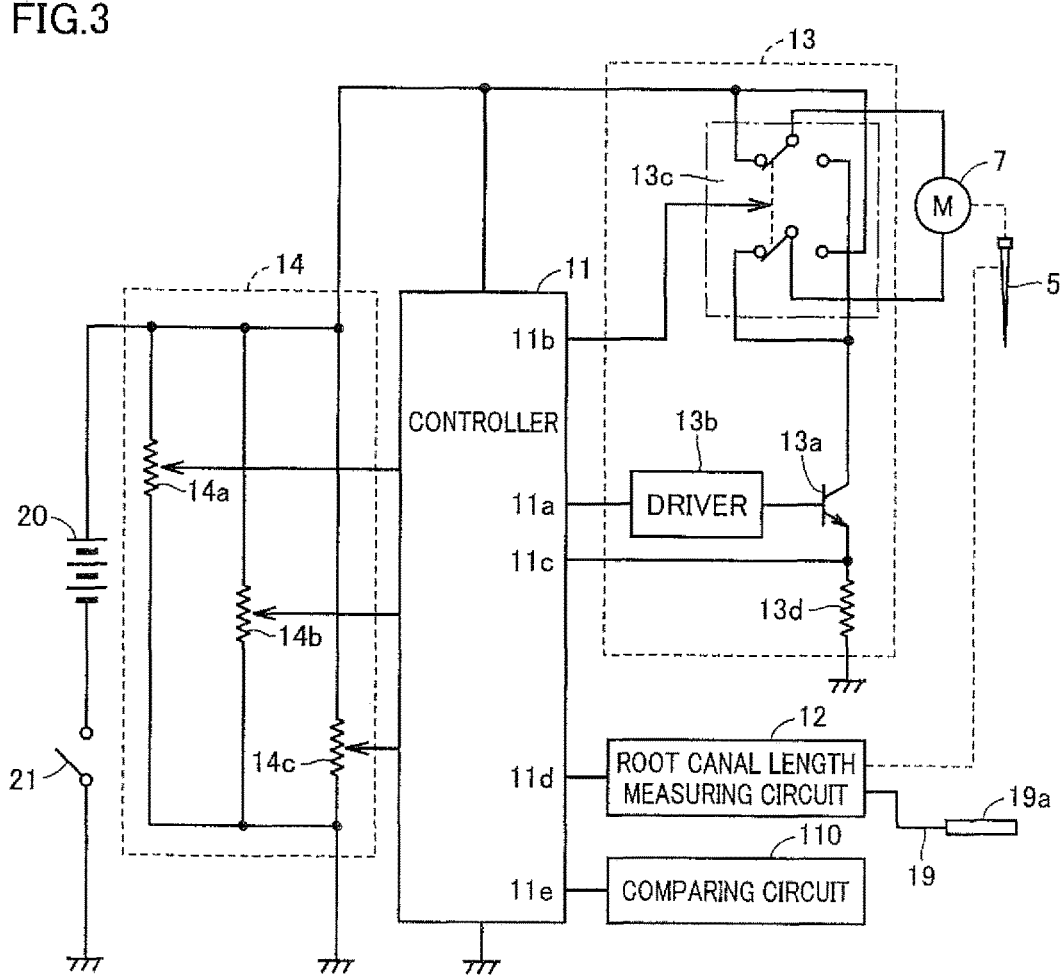
FIG. 3 is a circuit diagram showing a circuit configuration of the root canal treating device according to the first embodiment of the present invention.

Next, a circuit configuration of root canal treating device 100 for performing the driving control on cutting tool 5 is described in more detail. FIG. 3 is a circuit diagram showing a circuit configuration of root canal treating device 100 according to the first embodiment of the present invention. In root canal treating device 100 shown in FIG. 3, components of micro motor 7, controller 11, root canal length measuring circuit 12, motor driver 13, and setting unit 14 that are involved in the driving control on cutting tool 5 are illustrated.

Furthermore, motor driver 13 includes a transistor switch 13*a*, a transistor driver circuit 13*b*, a rotation direction switching switch 13*c*, and a resistor 13*d* for load detection. Setting unit 14 includes a variable resistor 14*a* for setting the reference load, a variable resistor 14*b* for setting a duty, and a variable resistor 14*c* for setting the reference position. Although setting unit 14 includes a configuration for setting the rotation angle (or rotation time) indicating the interval of comparing the detected load and the reference load in comparing circuit 110, or the like, this configuration is not shown in FIG. 3. A main power supply 20 and a main switch 21 are also connected to root canal treating device 100 shown in FIG. 3. Cutting tool 5 is held on micro motor 7 via an appropriate gear mechanism and the like, although not shown.

Transistor driver circuit 13*b* operates in response to a control signal outputted from a port 11*a* of controller 11, and controls ON/OFF of transistor switch 13*a* and drives micro motor 7. Micro motor 7 rotates in the normal rotation direction or in the reverse rotation direction in accordance with a state of rotation direction switching switch 13*c*. When the control signal outputted from port 11*a* of controller 11 has, for example, a pulse waveform repeated in a certain cycle, a width of the pulse waveform, that is, a duty ratio is adjusted by variable resistor 14*b* for setting a duty in setting unit 14. Micro motor 7 drives cutting tool 5 at the number of rotations corresponding to this duty ratio.

In response to a control signal outputted from a port 11*b* of controller 11, rotation direction switching switch 13*c* switches between driving cutting tool 5 in the normal rotation direction and driving cutting tool 5 in the reverse rotation direction. At a port 11*c*, controller 11 receives an amount of current (or voltage value) at a terminal of resistor 13*d* for load detection and detects a load applied to cutting tool 5. Therefore, resistor 13*d* for load detection functions as a load detecting unit for detecting the load applied to cutting tool 5. It should be noted that the load detecting unit is not limited to the configuration for detecting the load applied to cutting tool 5 based on the amount of current (or voltage value) at the terminal of resistor 13*d* for load detection. The load detecting unit may have another configuration such as a configuration for detecting the load applied to cutting tool 5 by using a torque sensor provided, for example, at a driving portion of cutting tool 5. The detected load is converted in controller 11 into, for example, a torque value applied to cutting tool 5, and is displayed on display unit 16. Comparing circuit 110 compares the torque value converted in controller 11 and a torque value set by variable resistor 14*a* for setting the reference load. As a matter of course, comparing circuit 110 may be configured to compare the amount of current (or voltage value) at the terminal of resistor 13*d* for load detection and the value set by setting unit 14, without conversion into the torque value.

Furthermore, controller 11 receives the root canal length measured by root canal length measuring circuit 12 at a port 11*d*. Therefore, root canal length measuring circuit 12 functions as a driving state detecting unit for detecting a position of the tip end of cutting tool 5 in the root canal. Controller 11 also outputs, from a port 11*e* to comparing circuit 110, the load applied to cutting tool 5 which has been detected by resistor 13*d* for load detection, and receives, from port 11*e*, a comparison result obtained by comparison with the reference load by comparing circuit 110. Therefore, comparing circuit 110 functions as a load comparing unit for comparing the load detected by the load detecting unit and the reference load.

Figure 4:
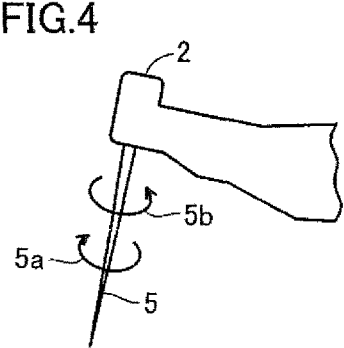
FIG. 4 is a schematic diagram showing a rotation direction of a cutting tool in the case of twist driving.

FIG. 4 is a schematic diagram showing the rotation direction of cutting tool 5. FIG. 4 shows driving in the normal rotation 5*a* direction for rotating cutting tool 5 clockwise as directed toward the tip end of cutting tool 5, and driving in the reverse rotation 5*b* direction for rotating cutting tool 5 counterclockwise. It should be noted that twist driving is driving for alternately performing the driving in the normal rotation 5*a* direction and the driving in the reverse rotation 5*b* direction.

Figure 5:
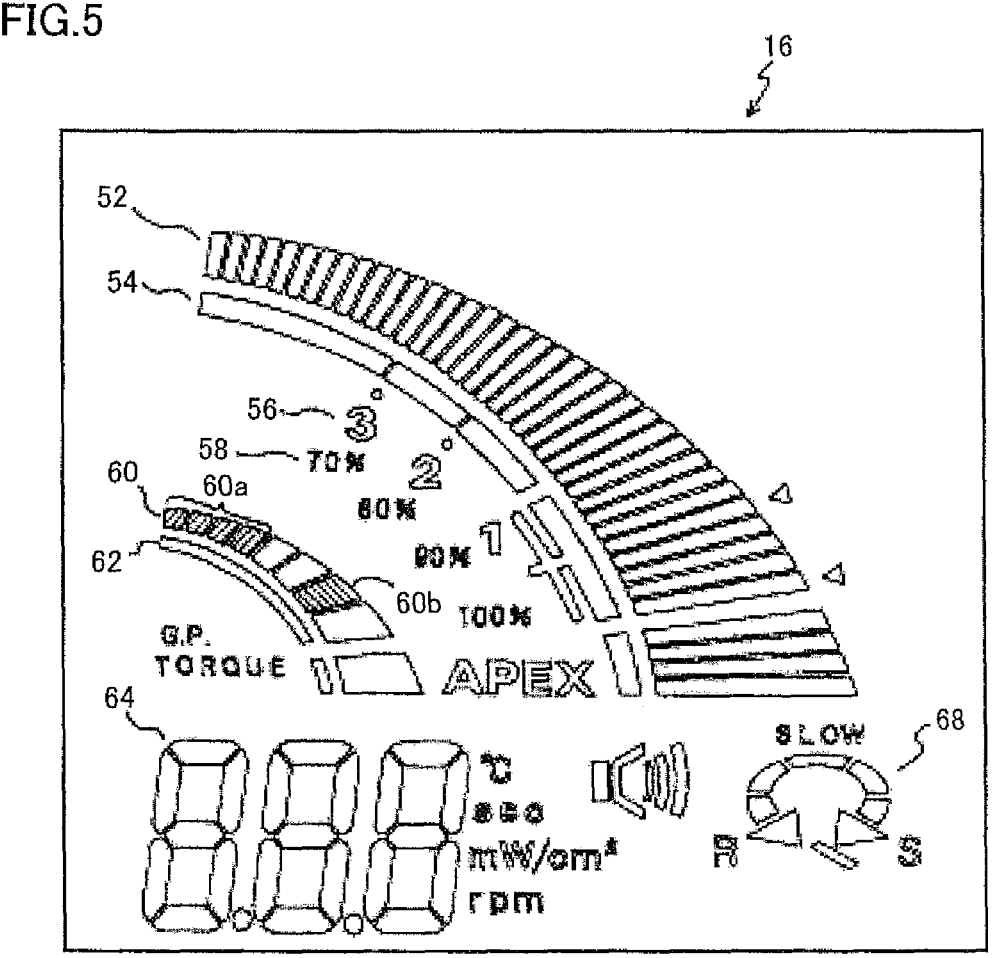
FIG. 5 is a diagram showing a display example of a liquid crystal display panel of a display unit shown in FIG. 1.

Next, display of a liquid crystal display panel of display unit 16 shown in FIG. 1 is described. FIG. 5 is a diagram showing a display example of the liquid crystal display panel of display unit 16 shown in FIG. 1.

Display unit 16 shown in FIG. 5 is the liquid crystal display panel, and is provided with a dot display unit 52 including many elements for displaying the measured root canal length in detail, a zone display unit 54 for dividing the root canal length into a plurality of zones and displaying the root canal length in a stepwise manner, a boundary display unit 56 for displaying a boundary of each zone, and an arrival rate display unit 58 for displaying a rate of arrival at the root apex.

Dot display unit 52 is configured such that the elements are sequentially displayed from the top to the bottom as the tip end of cutting tool 5 comes closer to the root apex. A position of the gauge "APEX" shows a position of the root apex, and arrival of the elements at this gauge means that the tip end of cutting tool 5 has nearly arrived at the position of the root apex.

Display unit 16 is also provided with a dot display unit 60 including many elements for displaying the load detected by resistor 13*d* for load detection (refer to FIG. 3), and a zone display unit 62 for dividing the load into a plurality of zones and displaying the load in a stepwise manner. Dot display unit 60 is configured such that the elements are sequentially displayed from the top to the bottom as the load detected by resistor 13*d* for load detection becomes larger.

For example, the load applied to cutting tool 5 when cutting tool 5 is cutting the tooth is displayed on dot display unit 60 by diagonally shaded elements 60*a*. In order to prevent frequent switching of displays, dot display unit 60 may have a peak hold function to display, for a certain time period, a maximum value of the load detected within a prescribed time period.

An element 60*b* corresponding to the reference load set by variable resistor 14*a* for setting the reference load (refer to FIG. 3) may also be displayed on dot display unit 60. By displaying element 60*b* on dot display unit 60, it is possible to visualize how much margin is present in the load detected by resistor 13*d* for load detection with respect to the reference load.

Display unit 16 is further provided with a numerical value display unit 64 for numerically displaying the number of rotations of cutting tool 5 and the load applied to cutting tool 5, and a rotation display unit 68 for displaying the orientation of rotation of cutting tool 5 (normal rotation, reverse rotation) and the number of rotations of cutting tool 5.

Next, driving of cutting tool 5 of root canal treating device 100 according to the first embodiment will be described. In root canal treating device 100 according to the first embodiment, the driving for rotating the cutting tool in the normal rotation direction by the predetermined rotation angle or for the predetermined rotation time is performed, and then, comparing circuit 110 compares the load applied to cutting tool 5 which has been detected by resistor 13*d* for load detection (hereinafter, also simply referred to as "detected load") and the reference load. When the detected load is, for example, equal to or larger than the reference load as a result of comparison by comparing circuit 110, controller 11 executes control to perform the driving for rotating, in the reverse rotation direction, cutting tool 5 that is being controlled to perform the driving for rotating cutting tool 5 in the normal rotation direction. Controller 11 may be configured to execute control to perform the driving for rotating, in the reverse rotation direction, cutting tool 5 that is being driven to be rotated in the normal rotation direction, when the detected load is, for example, larger than the reference load as a result of comparison by comparing circuit 110.

Figure 6:
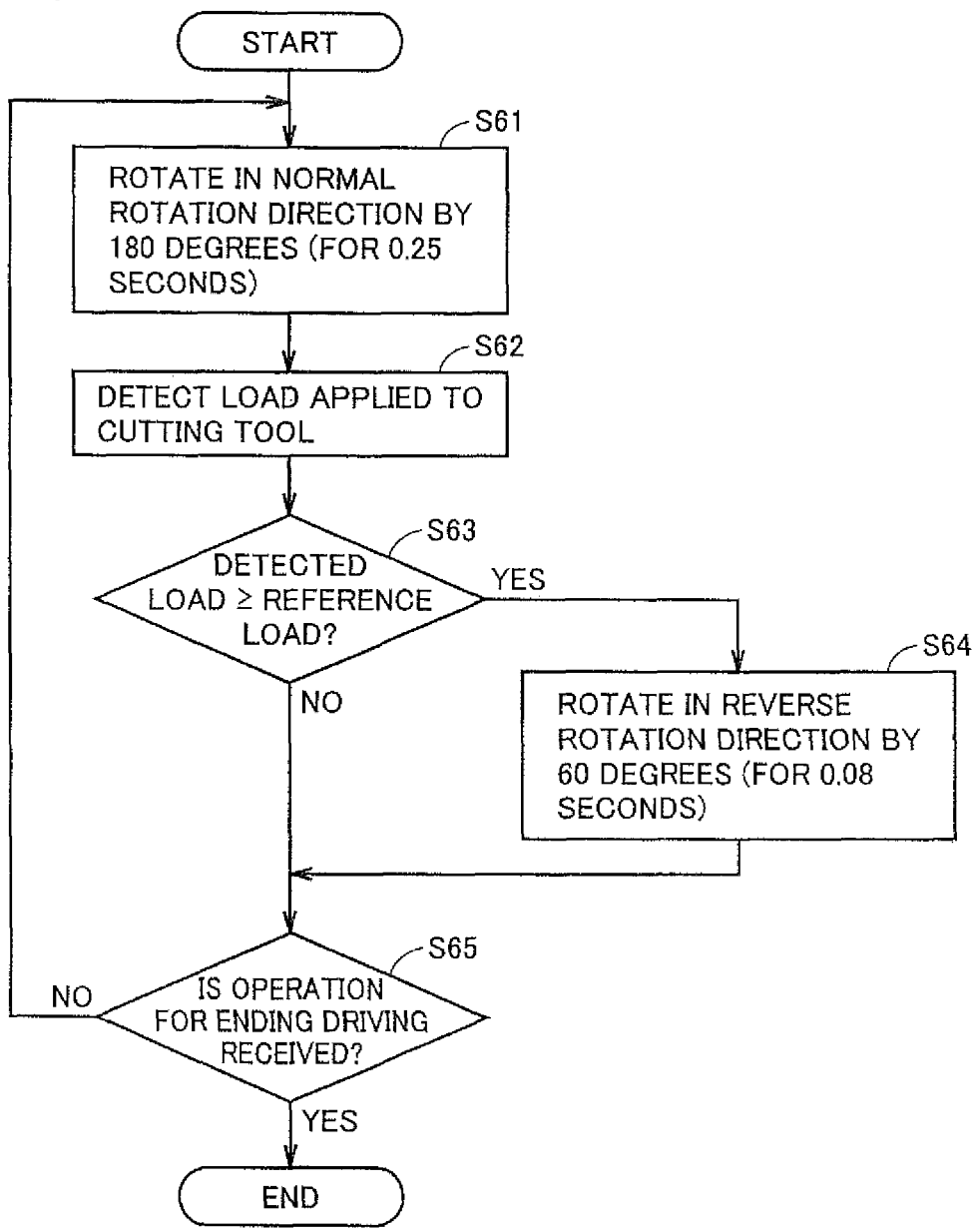
FIG. 6 is a flowchart for describing one example of driving of the cutting tool of the root canal treating device according to the first embodiment of the present invention.

FIG. 6 is a flowchart for describing one example of driving of cutting tool 5 of root canal treating device 100 according to the first embodiment of the present invention. First, controller 11 executes control to maintain the rotation direction of cutting tool 5 in the normal rotation direction until the driving for rotating cutting tool 5 in the normal rotation direction by motor driver 13 satisfies the predetermined rotation angle (e.g., 180 degrees) (during the normal rotation period) (step S61). Here, as a result of the driving in step S61, controller 11 does not necessarily need to rotate cutting tool 5 in the normal rotation direction by the predetermined rotation angle, and the driving force for rotating cutting tool 5 in the normal rotation direction by the predetermined rotation angle may only be supplied to motor driver 13. Even when the driving force for rotating cutting tool 5 by the predetermined rotation angle is supplied, the actual rotation angle of cutting tool 5 may vary depending on the situation of cutting the tooth. Initial values set in controller 11 are used as the number of rotations in the normal rotation direction (hereinafter, also simply referred to as "the number of normal rotations") and the number of rotations in the reverse rotation direction (hereinafter, also simply referred to as "the number of reverse rotations"), and they are not changed in the process in the flowchart shown in FIG. 6. In step S61, controller 11 may also execute control to maintain the rotation direction of cutting tool 5 in the normal rotation direction until the driving for rotating cutting tool 5 in the normal rotation direction by motor driver 13 satisfies the predetermined rotation time (e.g., 0.25 seconds) (during the normal rotation period). Namely, controller 11 may execute control to maintain the rotation direction of cutting tool 5 in the normal rotation direction during the normal rotation period until the driving for rotating cutting tool 5 in the normal rotation direction by motor driver 13 satisfies the predetermined condition (first condition). In addition to the rotation angle or the rotation time, the predetermined condition (first condition) may be defined by the amount of current or the voltage value supplied to micro motor 7, the value of the control signal supplied to motor driver 13, or the like.

Next, by using resistor 13*d* for load detection, controller 11 detects the load applied to cutting tool 5 when cutting tool 5 is rotated in the normal rotation direction by 180 degrees (step S62). In the description of the configuration of root canal treating device 100 according to the first embodiment, resistor 13*d* for load detection detects the load applied to cutting tool 5, after cutting tool 5 is rotated in the normal rotation direction by 180 degrees. The present invention is not, however, limited thereto. Resistor 13*d* for load detection may detect the load applied to cutting tool 5 at any point in time during rotation of cutting tool 5 in the normal rotation direction by 180 degrees. Furthermore, a maximum value or an average value of the load or at least one of a plurality of load values detected by resistor 13*d* for load detection during rotation by 180 degrees (or for 0.25 seconds) (during rotation by the predetermined rotation angle or for the predetermined rotation time) may be used as the load applied to cutting tool 5. As a result, appropriate detection of the load applied to cutting tool 5, which is required to prevent breakage of the cutting tool, becomes possible.

Next, comparing circuit 110 compares the load detected by resistor 13*d* for load detection and the reference load set by variable resistor 14*a* for setting the reference load in setting unit 14 (step S63). As a result, it is possible to detect cutting into the root canal wall by cutting tool 5, which is one cause of breakage of cutting tool 5. If the detected load is equal to or larger than the reference load (YES in step S63), controller 11 executes control to maintain the rotation direction of cutting tool 5 in the reverse rotation direction until the driving for rotating cutting tool 5 in the reverse rotation direction by motor driver 13 satisfies the predetermined reverse rotation angle (e.g., 60 degrees) or the predetermined reverse rotation time (e.g., about 0.08 seconds) (during a reverse rotation period) (step S64). Here, as a result of the driving in step S64, controller 11 does not necessarily need to rotate cutting tool 5 in the reverse rotation direction by the predetermined reverse rotation angle, and the driving force for rotating cutting tool 5 in the reverse rotation direction by the predetermined reverse rotation angle may only be supplied to motor driver 13. Even when the driving force for rotating cutting tool 5 by the predetermined reverse rotation angle is supplied, the actual reverse rotation angle of cutting tool 5 may vary depending on the situation of cutting the tooth.

In root canal treating device 100 according to the first embodiment, the process in steps S61 to S64 is performed, and thereby, comparing circuit 110 compares the load detected by resistor 13*d* for load detection and the reference load each time motor driver 13 drives cutting tool 5 in the normal rotation direction by the predetermined rotation angle or for the predetermined rotation time. Then, when the result of comparison by comparing circuit 110 attains a predetermined result (e.g., when the detected load is equal to or larger than the reference load), controller 11 controls the rotation direction of cutting tool 5 driven by motor driver 13 to the reverse rotation direction. Here, in the description of the configuration of root canal treating device 100 according to the first embodiment, the load applied to cutting tool 5 is detected each time motor driver 13 drives cutting tool 5 to be rotated in the normal rotation direction by 180 degrees, and comparing circuit 110 compares the detected load and the reference load. The present invention is not, however, limited thereto. Root canal treating device 100 according to the present invention may be configured such that the load applied to cutting tool 5 is detected at any timing during the normal rotation period until the driving for rotating cutting tool 5 in the normal rotation direction by motor driver 13 satisfies the predetermined rotation angle or the predetermined rotation time, and the detected load and the reference load are compared. As a result, comparing circuit 110 can start the process of comparing the detected load and the reference load, without waiting for the process of driving cutting tool 5 in the normal rotation direction by the predetermined rotation angle or for the predetermined rotation time by motor driver 13 (step S61) to be completed. Therefore, cutting tool 5 can be driven efficiently.

Controller 11 also executes control to perform the driving for rotating cutting tool 5 in the normal rotation direction by 180 degrees and in the reverse rotation direction by 60 degrees. Namely, the rotation angle or the rotation time for rotating cutting tool 5 in the normal rotation direction is set to be larger than the reverse rotation angle or the reverse rotation time for rotating cutting tool 5 in the reverse rotation direction. Particularly, the rotation angle or the rotation time for rotating cutting tool 5 in the normal rotation direction is desirably one-half or larger of the reverse rotation angle or the reverse rotation time for rotating cutting tool 5 in the reverse rotation direction. As a result, in root canal treating device 100, the rotation angle or the rotation time in the normal rotation direction that contributes to cutting of the tooth is set to be larger than the reverse rotation angle or the reverse rotation time in the reverse rotation direction that does not contribute to cutting of the tooth, and thus, the tooth cutting efficiency can be enhanced. In order to further reduce the load applied to cutting tool 5 at the expense of the tooth cutting efficiency, the reverse rotation angle or the reverse rotation time for rotating cutting tool 5 in the reverse rotation direction may be brought closer to or may be set to be the same as the rotation angle or the rotation time for rotating cutting tool 5 in the normal rotation direction.

If the detected load is smaller than the reference load (NO in step S63), or after cutting tool 5 is rotated in the reverse rotation direction by 60 degrees (step S64), controller 11 determines whether the operation for ending the driving is received from operation unit 15 or not (step S65). If the operation for ending the driving is received from operation unit 15 (YES in step S65), controller 11 ends the driving. If the operation for ending the driving is not received from operation unit 15 (NO in step S65), the process returns to step S61 and controller 11 drives cutting tool 5 to be rotated in the normal rotation direction by 180 degrees.

In root canal treating device 100 according to the first embodiment, cutting tool 5 is driven to rotate in the reverse rotation direction by 60 degrees (step S64), and thereafter, cutting tool 5 is driven back to rotate in the normal rotation direction by 180 degrees (step S61). As a result, in root canal treating device 100 according to the first embodiment, cutting tool 5 is not continuously driven in the reverse rotation direction and the rotation in the normal rotation direction that contributes to cutting of the tooth is reliably performed after the rotation in the reverse rotation direction, and thus, the efficiency of the work for cutting and enlarging the root canal of the tooth can be improved.

Figure 7:
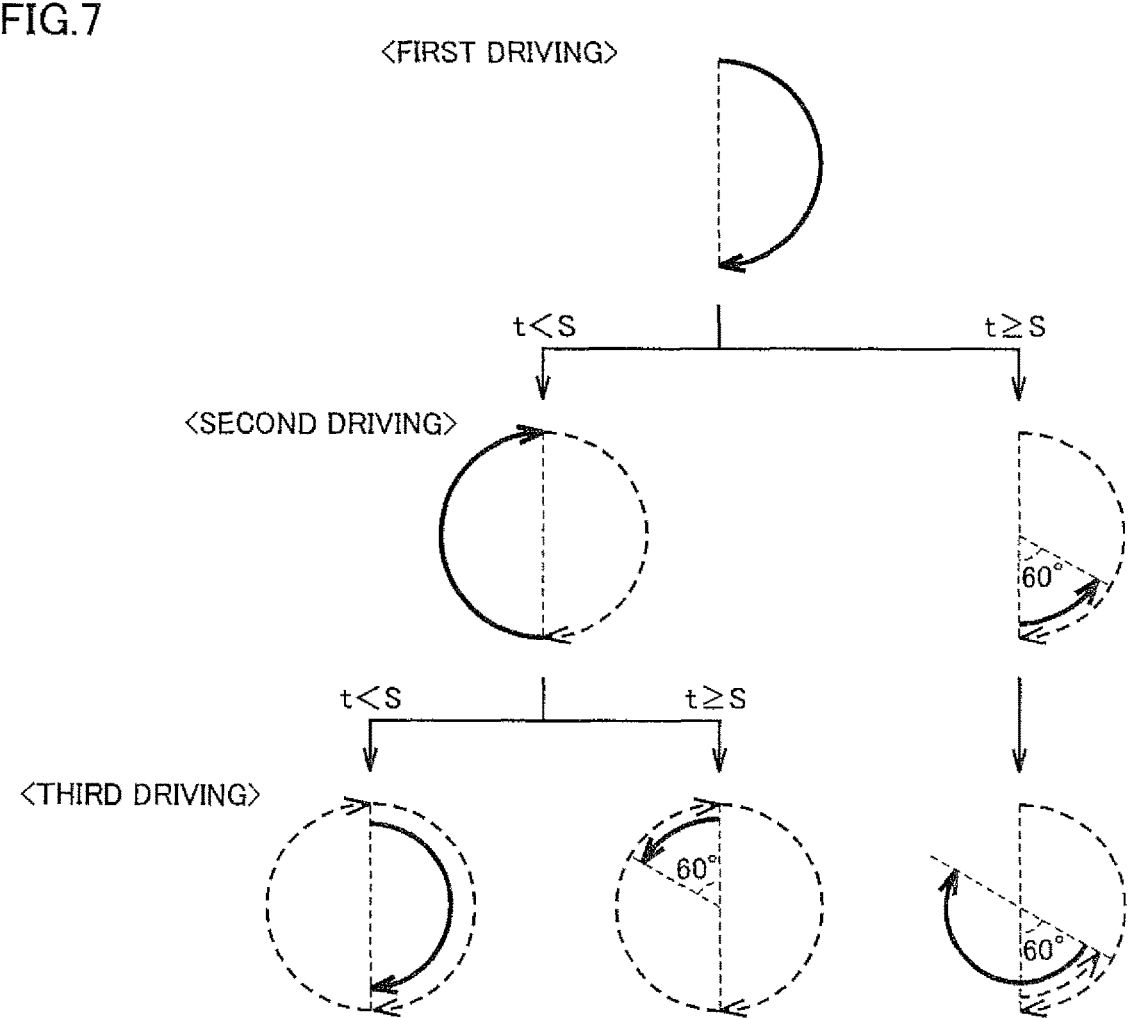
FIG. 7 is a schematic diagram for describing one example of driving of the cutting tool of the root canal treating device according to the first embodiment of the present invention.

Description will be given to how controller 11 drives cutting tool 5 as a result of the driving in accordance with the flowchart shown in FIG. 6. FIG. 7 is a schematic diagram for describing one example of driving of cutting tool 5 of root canal treating device 100 according to the first embodiment of the present invention. A clockwise arrow shown in FIG. 7 indicates that cutting tool 5 is driven in the normal rotation direction, and an angle formed by the clockwise arrow indicates a rotation angle for rotating cutting tool 5 in the normal rotation direction. On the other hand, a counterclockwise arrow indicates that cutting tool 5 is driven in the reverse rotation direction, and an angle formed by the counterclockwise arrow indicates a rotation angle for rotating cutting tool 5 in the reverse rotation direction. In the following description with reference to FIG. 7, driving until determination of whether to switch the driving direction or not is made based on the comparison result by comparing circuit 110, or driving until the driving direction is switched, is defined as one driving.

First, in the first driving, controller 11 executes control to perform the driving for rotating cutting tool 5 in the normal rotation direction by 180 degrees (corresponding to step S61 shown in FIG. 6). In accordance with a result of comparison between a detected load t and a reference load s by comparing circuit 110, the second driving has two types of drivings. Specifically, if detected load t is smaller than reference load s (t<s) (corresponding to NO in step S63 shown in FIG. 6), controller 11 executes control to perform the driving for rotating cutting tool 5 in the normal rotation direction by 180 degrees (corresponding to step S61 shown in FIG. 6). As a result, controller 11 has executed control such that cutting tool 5 makes one normal rotation. On the other hand, if detected load t is equal to or larger than reference load s (t≥s) (corresponding to YES in step S63 shown in FIG. 6), controller 11 executes control to perform the driving for rotating cutting tool 5 in the reverse rotation direction by 60 degrees (corresponding to step S64 shown in FIG. 6). As a result, controller 11 has executed control to perform the driving such that cutting tool 5 makes one-half rotation in the normal rotation direction and one-sixth rotation in the reverse rotation direction.

In the third driving, different driving is performed in accordance with whether cutting tool 5 has been driven in the normal rotation direction or cutting tool 5 has been driven in the reverse rotation direction in the second driving. First, when cutting tool 5 has been driven in the normal rotation direction in the second driving, the third driving has two types of drivings in accordance with a result of comparison between detected load t and reference load s by comparing circuit 110, similarly to the second driving.

Specifically, if detected load t is smaller than reference load s (t<s), controller 11 executes control to perform the driving for rotating cutting tool 5 in the normal rotation direction by 180 degrees (corresponding to step S61 shown in FIG. 6). As a result, controller 11 has executed control such that cutting tool 5 makes one and a half rotations in the normal rotation direction. On the other hand, if detected load t is equal to or larger than reference load s (t≥s), controller 11 executes control to perform the driving for rotating cutting tool 5 in the reverse rotation direction by 60 degrees (corresponding to step S64 shown in FIG. 6). As a result, controller 11 has executed control to perform the driving such that cutting tool 5 makes one rotation in the normal rotation direction and one-sixth rotation in the reverse rotation direction.

When cutting tool 5 has been driven in the reverse rotation direction in the second driving, controller 11 executes control to perform the driving for rotating cutting tool 5 in the normal rotation direction by 180 degrees, without further driving cutting tool 5 in the reverse rotation direction (corresponding to step S61 shown in FIG. 6). As a result, controller 11 has executed control such that cutting tool 5 makes one-half rotation in the normal rotation direction and one-sixth rotation in the reverse rotation direction, and thereafter, one-half rotation in the normal rotation direction. In the fourth and subsequent drivings, the drivings described in the first to third drivings are repeated, and thus, description will not be repeated.

As described above, in root canal treating device 100 according to the first embodiment, controller 11 maintains the rotation direction of cutting tool 5 in the normal rotation direction during the normal rotation period until the driving for rotating cutting tool 5 in the normal rotation direction by motor driver 13 satisfies the predetermined rotation angle or the predetermined rotation time. When the load detected by resistor 13*d* for load detection and the reference load are compared during the normal rotation period and the detected load is equal to or larger than the reference load, controller 11 controls the rotation direction of cutting tool 5 to the reverse rotation direction. Therefore, in root canal treating device 100 according to the first embodiment, breakage of the cutting tool due to the applied load can be prevented. In addition, the cutting tool can continue to be rotated in the normal rotation direction in accordance with the comparison result, and thus, the tooth cutting efficiency can be enhanced as compared with the twist driving in which cutting tool 5 is rotated in the normal rotation direction and thereafter is rotated in the reverse rotation direction without exception. Furthermore, in root canal treating device 100 according to the first embodiment, cutting tool 5 is reliably rotated in the normal rotation direction to perform the driving that contributes to cutting of the tooth. Therefore, the efficiency of the work for cutting and enlarging the root canal of the tooth can be improved. Controller 11 is not limited to executing control for directly changing the rotation direction of cutting tool 5 from the normal rotation direction to the reverse rotation direction, and may execute control for temporarily stopping the rotation of cutting tool and thereafter changing the rotation direction of cutting tool 5 from the normal rotation direction to the reverse rotation direction.

In the description of root canal treating device 100 according to the first embodiment, the predetermined rotation angle is set at 180 degrees and the predetermined reverse rotation angle is set at 60 degrees. The present invention is not, however, limited thereto. The predetermined rotation angle may be, for example, 360 degrees or 720 degrees and the predetermined reverse rotation angle may be, for example, 120 degrees or 240 degrees. In addition, in root canal treating device 100 according to the first embodiment, the initial values set in controller 11 are used as the number of normal rotations and the number of reverse rotations, and no mention is particularly made of whether the number of normal rotations and the number of reverse rotations are the same or not. However, setting unit 14 may set the number of reverse rotations to be larger than the number of normal rotations. Namely, controller 11 controls cutting tool 5 such that the rotation speed when cutting tool 5 is rotated in the reverse rotation direction is higher than the rotation speed when cutting tool 5 is rotated in the normal rotation direction. As a result, in root canal treating device 100 according to the first embodiment, the time of driving for rotating cutting tool 5 in the reverse rotation direction that does not contribute to cutting of the tooth is shortened, and thereby, the efficiency of the work for cutting and enlarging the root canal of the tooth can be improved.

(Modification)

In the flowchart shown in FIG. 6, in step S61, controller 11 executes control to maintain the rotation direction of cutting tool 5 in the normal rotation direction until the driving for rotating cutting tool 5 in the normal rotation direction by motor driver 13 satisfies the predetermined rotation angle (e.g., 180 degrees) or the predetermined rotation time (e.g., 0.25 seconds) (during the normal rotation period). Thereafter, in step S63, comparing circuit 110 compares the detected load and the set reference load. Root canal treating device 100 according to the first embodiment is not, however, limited thereto. Controller 11 does not execute control to maintain the rotation direction of cutting tool 5 in the normal rotation direction during the normal rotation period, but may only execute control to perform driving for continuously rotating cutting tool 5 in the normal rotation direction during the normal rotation period. Namely, root canal treating device 100 according to the first embodiment may be configured such that comparing circuit 110 compares the detected load and the set reference load at a timing at which cutting tool 5 rotating continuously in the normal rotation direction rotates by the predetermined rotation angle or for the predetermined rotation time.

Figure 8:
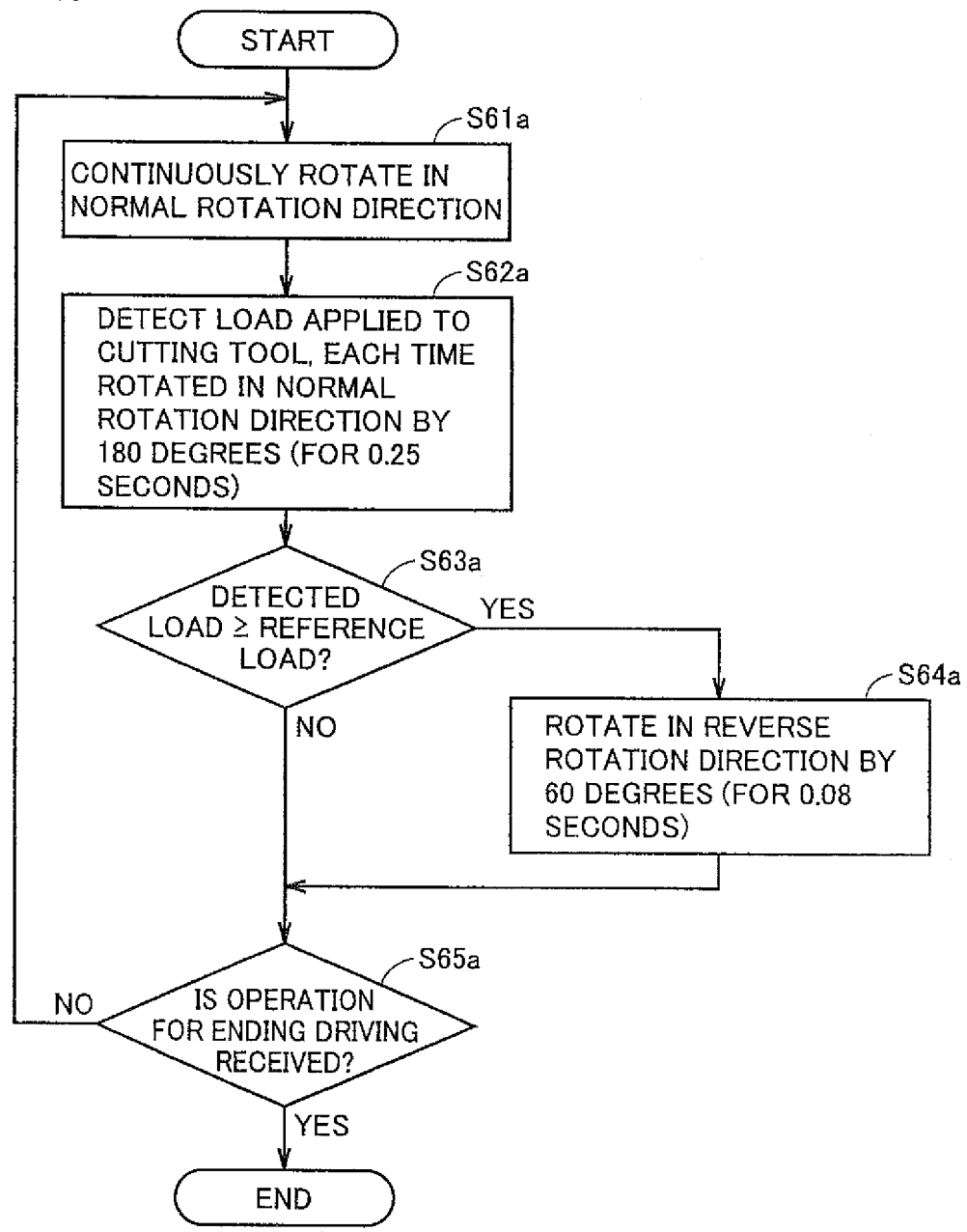
FIG. 8 is a flowchart for describing one example of driving of a cutting tool of a root canal treating device according to a modification of the first embodiment of the present invention.

Specific description will be given to a modification in which control is executed to perform the driving for continuously rotating cutting tool 5 in the normal rotation direction. FIG. 8 is a flowchart for describing one example of driving of cutting tool 5 of root canal treating device 100 according to a modification of the first embodiment of the present invention. First, controller 11 executes control to perform the driving for continuously rotating cutting tool 5 in the normal rotation direction by motor driver 13 (step S61*a*). The initial values set in controller 11 are used as the number of normal rotations and the number of reverse rotations, and they are not changed in the process in the flowchart shown in FIG. 8.

Next, by using resistor 13*d* for load detection, controller 11 detects the load applied to cutting tool 5, when cutting tool 5 is rotated in the normal rotation direction by the predetermined rotation angle or for the predetermined rotation time (step S62*a*). Resistor 13*d* for load detection may detect the load applied to cutting tool 5 at any point in time during rotation of cutting tool 5 in the normal rotation direction by 180 degrees, or a maximum value or an average value of the detected load or at least one of a plurality of detected load values may be used.

Next, comparing circuit 110 compares the load detected by resistor 13*d* for load detection and the reference load set by variable resistor 14a for setting the reference load in setting unit 14, when cutting tool 5 is rotated in the normal rotation direction by the predetermined rotation angle or for the predetermined rotation time (step S63a). As a result, it is possible to detect cutting into the root canal wall by cutting tool 5, which is one cause of breakage of cutting tool 5. If the detected load is equal to or larger than the reference load (YES in step S63a), controller 11 executes control to maintain the rotation direction of cutting tool 5 in the reverse rotation direction until the driving for rotating cutting tool 5 in the reverse rotation direction by motor driver 13 satisfies the predetermined reverse rotation angle (e.g., 60 degrees) or the predetermined rotation time (e.g., about 0.08 seconds) (during the reverse rotation period) (step S64a). If the detected load is smaller than the reference load (NO in step S63a), or after cutting tool 5 is rotated in the reverse rotation direction by 60 degrees (step S64a), controller 11 determines whether the operation for ending the driving is received from operation unit 15 or not (step S65a). Since steps S64a and S65a shown in FIG. 8 are the same as steps S64 and S65 shown in FIG. 6, respectively, detailed description will not be repeated.

As described above, in root canal treating device 100 according to the modification of the first embodiment, in the case of continuously driving cutting tool 5 in the normal rotation direction, the load applied to cutting tool 5 and the reference load are compared each time cutting tool 5 is driven in the normal rotation direction by the predetermined rotation angle or for the predetermined rotation time, and when the load applied to cutting tool 5 is equal to or larger than the reference load, the rotation direction of cutting tool 5 is controlled to the reverse rotation direction. Therefore, also in root canal treating device 100 according to the modification of the first embodiment, breakage of the cutting tool due to the applied load can be prevented. In addition, the cutting tool can continue to be rotated in the normal rotation direction in accordance with the comparison result, and thus, the tooth cutting efficiency can be enhanced as compared with the twist driving in which cutting tool 5 is rotated in the normal rotation direction and thereafter is rotated in the reverse rotation direction without exception.

(Second Embodiment)

In the description of the configuration of root canal treating device 100 according to the first embodiment of the present invention, control is executed to perform the driving for rotating cutting tool 5 in the reverse rotation direction by 60 degrees, and then, control is executed to return to the driving for rotating cutting tool 5 in the normal rotation direction by 180 degrees. In accordance with a root canal treating device according to a second embodiment of the present invention, such a configuration will be described that control is executed to perform the driving for rotating the cutting tool in the reverse rotation direction by 60 degrees, and thereafter, control is executed to perform the driving for further rotating the cutting tool in the reverse rotation direction by 60 degrees when the detected load is equal to or larger than the reference load.

Since the root canal treating device according to the second embodiment has the same configuration as that of root canal treating device 100 according to the first embodiment shown in FIGS. 1 to 3, the same reference characters are used and detailed description will not be repeated.

Figure 9:
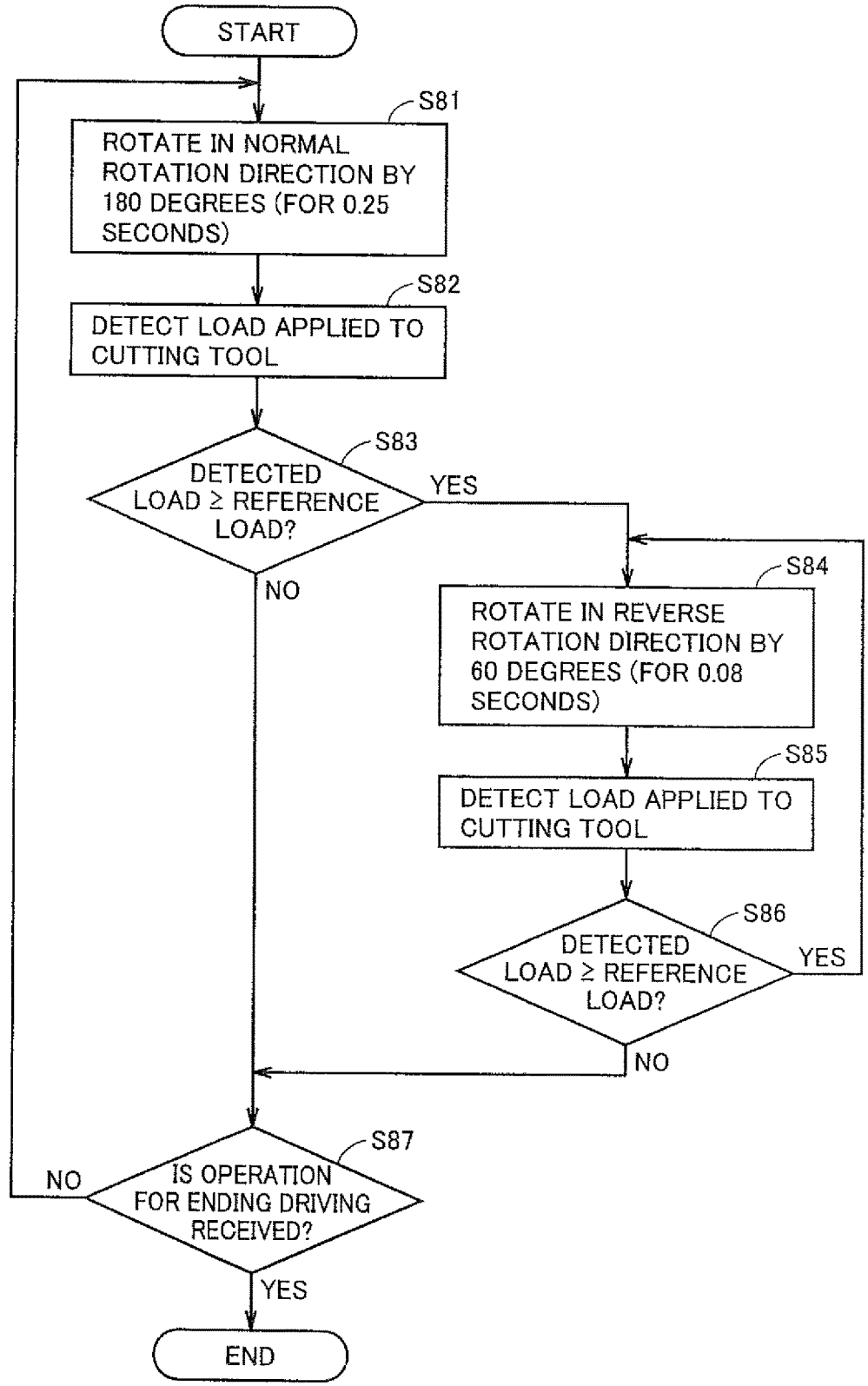
FIG. 9 is a flowchart for describing one example of driving of a cutting tool of a root canal treating device according to a second embodiment of the present invention.

FIG. 9 is a flowchart for describing one example of driving of cutting tool 5 of root canal treating device 100 according to the second embodiment of the present invention. First, controller 11 executes control to maintain the rotation direction of cutting tool 5 in the normal rotation direction until the driving for rotating cutting tool 5 in the normal rotation direction by motor driver 13 satisfies the predetermined rotation angle (e.g., 180 degrees) (during the normal rotation period) (step S81). Here, as a result of the driving in step S81, controller 11 does not necessarily need to rotate cutting tool 5 in the normal rotation direction by the predetermined rotation angle, and the driving force for rotating cutting tool 5 in the normal rotation direction by the predetermined rotation angle may only be supplied to motor driver 13. Even when the driving force for rotating cutting tool 5 by the predetermined rotation angle is supplied, the actual rotation angle of cutting tool 5 may vary depending on the situation of cutting the tooth. The initial values set in controller 11 are used as the number of normal rotations and the number of reverse rotations, and they are not changed in the process in the flowchart shown in FIG. 9. In step S81, controller 11 may also execute control to maintain the rotation direction of cutting tool 5 in the normal rotation direction until the driving for rotating cutting tool 5 in the normal rotation direction by motor driver 13 satisfies the predetermined rotation time (e.g., 0.25 seconds) (during the normal rotation period). Namely, controller 11 may execute control to maintain the rotation direction of cutting tool 5 in the normal rotation direction during the normal rotation period until the driving for rotating cutting tool 5 in the normal rotation direction by motor driver 13 satisfies the predetermined condition (first condition). In addition to the rotation angle or the rotation time, the predetermined condition (first condition) may be defined by the amount of current or the voltage value supplied to micro motor 7, the value of the control signal supplied to motor driver 13, or the like.

Next, by using resistor 13d for load detection, controller 11 detects the load applied to cutting tool 5 when cutting tool 5 is rotated in the normal rotation direction by 180 degrees (step S82). In the description of the configuration of root canal treating device 100 according to the second embodiment, resistor 13d for load detection detects the load applied to cutting tool 5, after cutting tool 5 is rotated in the normal rotation direction by 180 degrees. The present invention is not, however, limited thereto. Resistor 13d for load detection may detect the load applied to cutting tool 5 at any point in time during rotation of cutting tool 5 in the normal rotation direction by 180 degrees. Furthermore, a maximum value or an average value of the load or at least one of a plurality of load values detected by resistor 13d for load detection during rotation by 180 degrees (or for 0.25 seconds) (during rotation by the predetermined rotation angle or for the predetermined rotation time) may be used as the load applied to cutting tool 5.

Next, comparing circuit 110 compares the load detected by resistor 13d for load detection and the reference load set by variable resistor 14a for setting the reference load in setting unit 14 (step S83). If the detected load is equal to or larger than the reference load (YES in step S83), controller 11 executes control to maintain the rotation direction of cutting tool 5 in the reverse rotation direction until the driving for rotating cutting tool 5 in the reverse rotation direction by motor driver 13 satisfies the predetermined reverse rotation angle (e.g., 60 degrees) or the predetermined reverse rotation time (e.g., about 0.08 seconds) (during the reverse rotation period) (step S84). Namely, controller 11 may execute control to maintain the rotation direction of cutting tool 5 in the reverse rotation direction during the reverse rotation period until the driving for rotating cutting tool 5 in the reverse rotation direction by motor driver 13 satisfies a predetermined condition (second condition). In addition to the reverse rotation angle or the reverse rotation time, the predetermined condition (second condition) may be defined by the amount of current or the voltage value supplied to micro motor 7, the value of the control signal supplied to motor driver 13, or the like. Here, as a result of the driving in step S84, controller 11 does not necessarily need to rotate cutting tool 5 in the reverse rotation direction by the predetermined reverse rotation angle, and the driving force for rotating cutting tool 5 in the reverse rotation direction by the predetermined reverse rotation angle may only be supplied to motor driver 13. Even when the driving force for rotating cutting tool 5 by the predetermined reverse rotation angle is supplied, the actual reverse rotation angle of cutting tool 5 may vary depending on the situation of cutting the tooth.

In root canal treating device 100 according to the second embodiment, the process in steps S81 to S84 is performed, and thereby, comparing circuit 110 compares the load detected by resistor 13d for load detection and the reference load each time motor driver 13 drives cutting tool 5 in the normal rotation direction by the predetermined rotation angle or for the predetermined rotation time. Then, when the result of comparison by comparing circuit 110 attains a predetermined result (e.g., when the detected load is equal to or larger than the reference load), controller 11 maintains the rotation direction of cutting tool 5 in the reverse rotation direction until the driving for rotating cutting tool 5 in the reverse rotation direction by motor driver 13 satisfies the predetermined reverse rotation angle or the predetermined reverse rotation time (during the reverse rotation period). Here, in the description of the configuration of root canal treating device 100 according to the second embodiment, the load applied to cutting tool 5 is detected each time motor driver 13 drives cutting tool 5 to be rotated in the normal rotation direction by 180 degrees, and comparing circuit 110 compares the load and the reference load. The present invention is not, however, limited thereto. Root canal treating device 100 according to the second embodiment may be configured to detect the load applied to cutting tool 5 at any timing during rotation of cutting tool 5 in the normal rotation direction by the predetermined rotation angle or for the predetermined rotation time by motor driver 13, and to compare the detected load and the reference load.

Next, by using resistor 13d for load detection, controller 11 detects the load applied to cutting tool 5 when cutting tool 5 is rotated in the reverse rotation direction by 60 degrees (step S85). In the description of the configuration of root canal treating device 100 according to the second embodiment, resistor 13d for load detection detects the load applied to cutting tool 5, after cutting tool 5 is rotated in the reverse rotation direction by 60 degrees. The present invention is not, however, limited thereto. Resistor 13d for load detection may detect the load applied to cutting tool 5 at any point in time during rotation of cutting tool 5 in the reverse rotation direction by 60 degrees. Furthermore, a maximum value or an average value of the load or at least one of a plurality of load values detected by resistor 13d for load detection during rotation by 60 degrees (or for about 0.08 seconds) (during rotation by the predetermined reverse rotation angle or for the predetermined reverse rotation time) may be used as the load applied to cutting tool 5. Regardless of the load applied to cutting tool 5 which has been detected in step S85, cutting tool 5 may be rotated in the normal rotation direction and the process may be returned to step S82.

Next, comparing circuit 110 compares the load detected by resistor 13d for load detection and the reference load set by variable resistor 14a for setting the reference load in setting unit 14 (step S86). If the detected load is equal to or larger than the reference load (YES in step S86), the process returns to step S84 and controller 11 further executes control to maintain the rotation direction of cutting tool 5 in the reverse rotation direction until the driving for rotating cutting tool 5 in the reverse rotation direction by motor driver 13 satisfies the predetermined reverse rotation angle (e.g., 60 degrees) or the predetermined reverse rotation time (e.g., about 0.08 seconds) (during the reverse rotation period).

In root canal treating device 100 according to the second embodiment, the process in steps S84 to S86 is performed, and thereby, comparing circuit 110 compares the load detected by resistor 13d for load detection and the reference load each time motor driver 13 drives cutting tool 5 in the reverse rotation direction by the predetermined reverse rotation angle or for the predetermined reverse rotation time. The present invention is not, however, limited thereto. Root canal treating device 100 according to the present invention may be configured to detect the load applied to cutting tool 5 at any timing during rotation of cutting tool 5 in the reverse rotation direction by 60 degrees by motor driver 13 (during rotation by the predetermined reverse rotation angle or for the predetermined reverse rotation time), and to compare the detected load and the reference load. When controller 11 executes control to perform the driving for further rotating cutting tool 5 in the reverse rotation direction, controller 11 may execute control to perform the driving for rotating cutting tool 5 by an angle different from 60 degrees, such as, for example, 30 degrees or 90 degrees.

In addition, in the description of root canal treating device 100 according to the second embodiment, the reference load compared with the load detected in step S83 (the load detected in the normal rotation direction) and the reference load compared with the load detected in step S86 (the load detected in the reverse rotation direction) are set to have the same value. The present invention is not, however, limited thereto. The reference load compared with the load detected in step S83 and the reference load compared with the load detected in step S86 may be set to have different values. As a result, root canal treating device 100 according to the second embodiment can have a high degree of freedom for setting the reference load and can perform various drivings. When the reference load compared with the load detected in step S86 and the reference load compared with the load detected in step S83 are set to have different values, the reference load compared with the load detected in step S86 is defined as a reverse rotation reference load.

If the detected load is smaller than the reference load (NO in steps S83 and S86), controller 11 determines whether the operation for ending the driving is received from operation unit 15 or not (step S87). If the operation for ending the driving is received from operation unit 15 (YES in step S87), controller 11 ends the driving. If the operation for ending the driving is not received from operation unit 15 (NO in step S87), the process returns to step S81 and controller 11 executes control to perform the driving for rotating cutting tool 5 in the normal rotation direction by 180 degrees.

Figure 10:
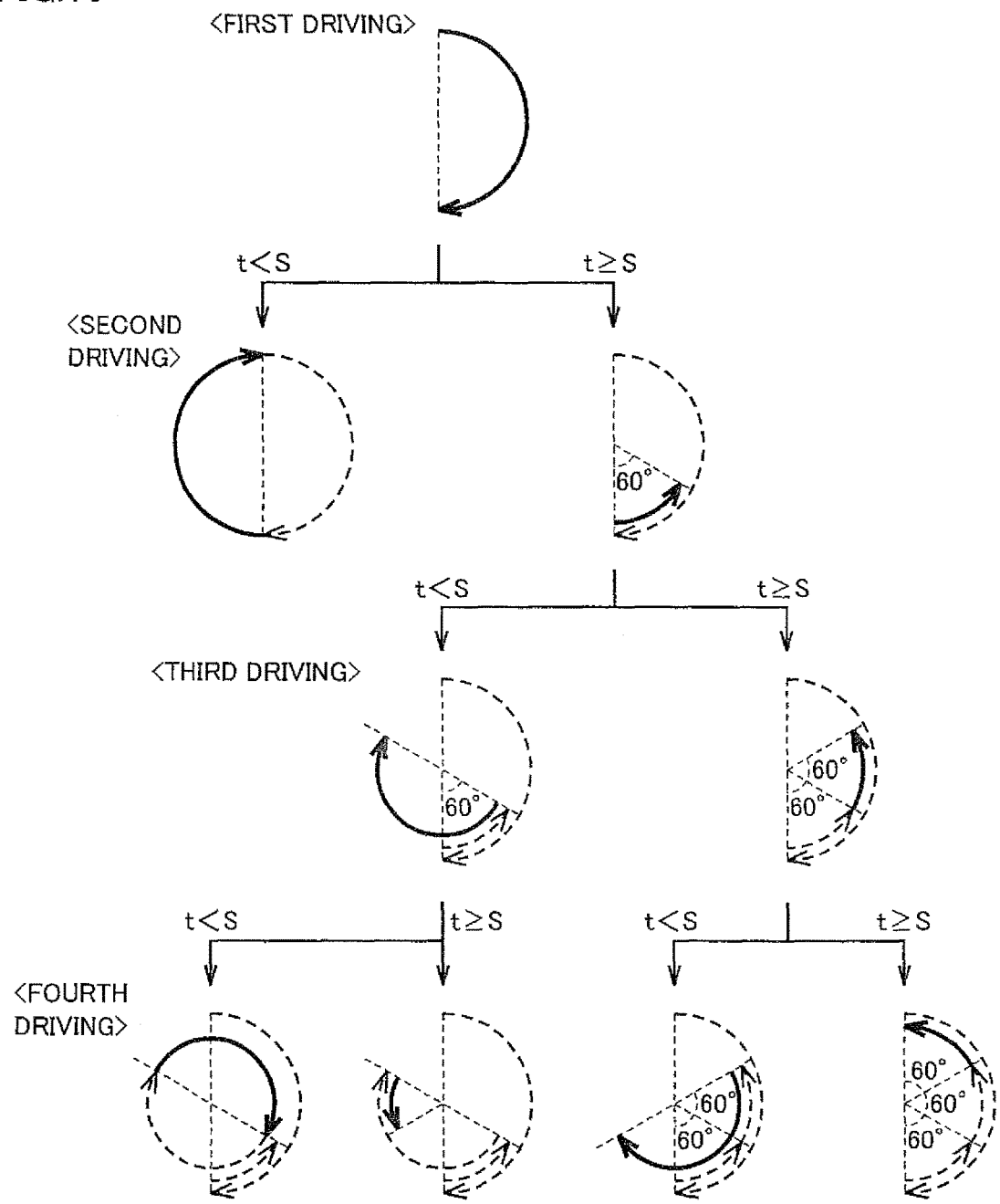
FIG. 10 is a schematic diagram for describing one example of driving of the cutting tool of the root canal treating device according to the second embodiment of the present invention.

Description will be given to how controller 11 drives cutting tool 5 as a result of the driving in accordance with the flowchart shown in FIG. 9. FIG. 10 is a schematic diagram for describing one example of driving of cutting tool 5 of root canal treating device 100 according to the second embodiment of the present invention. A clockwise arrow shown in FIG. 10 indicates that cutting tool 5 is driven in the normal rotation direction, and an angle formed by the clockwise arrow indicates a rotation angle for rotating cutting tool 5 in the normal rotation direction. On the other hand, a counterclockwise arrow indicates that cutting tool 5 is driven in the reverse rotation direction, and an angle formed by the counterclockwise arrow indicates a rotation angle for rotating cutting tool 5 in the reverse rotation direction. In the following description with reference to FIG. 10, driving until determination of whether to switch the driving direction or not is made based on the comparison result by comparing circuit 110, or driving until the driving direction is switched, is defined as one driving.

First, in the first driving, controller 11 executes control to perform the driving for rotating cutting tool 5 in the normal rotation direction by 180 degrees (corresponding to step S81 shown in FIG. 9). In accordance with a result of comparison between detected load t and reference load s by comparing circuit 110, the second driving has two types of drivings. Specifically, if detected load t is smaller than reference load s (t<s), controller 11 executes control to perform the driving for rotating cutting tool 5 in the normal rotation direction by 180 degrees (corresponding to step S81 shown in FIG. 9). As a result, controller 11 has driven cutting tool 5 such that cutting tool 5 makes one normal rotation. On the other hand, if detected load t is equal to or larger than reference load s (t≥s), controller 11 executes control to perform the driving for rotating cutting tool 5 in the reverse rotation direction by 60 degrees (corresponding to step S84 shown in FIG. 9). As a result, controller 11 has executed control to perform the driving such that cutting tool 5 makes one-half rotation in the normal rotation direction and one-sixth rotation in the reverse rotation direction.

In the third driving, different driving is performed in accordance with whether cutting tool 5 has been driven in the normal rotation direction or cutting tool 5 has been driven in the reverse rotation direction in the second driving. First, when cutting tool 5 has been driven in the normal rotation direction in the second driving, the same driving as the third driving described with reference to FIG. 7 is performed, and thus, illustration and description will not be repeated.

When cutting tool 5 has been driven in the reverse rotation direction in the second driving, the third driving has two types of drivings in accordance with a result of comparison between detected load t and reference load s by comparing circuit 110, similarly to the second driving. Specifically, if detected load t is smaller than reference load s (t<s), controller 11 executes control to perform the driving for rotating cutting tool 5 in the normal rotation direction by 180 degrees (corresponding to step S81 shown in FIG. 9). As a result, controller 11 has executed control to perform the driving such that cutting tool 5 makes one-half rotation in the normal rotation direction and one-sixth rotation in the reverse rotation direction, and thereafter, one-half rotation in the normal rotation direction. On the other hand, if detected load t is equal to or larger than reference load s (t≥s), controller 11 executes control to perform the driving for further rotating cutting tool 5 in the reverse rotation direction by 60 degrees (corresponding to step S84 shown in FIG. 9). As a result, controller 11 has executed control to perform the driving such that cutting tool 5 makes one-half rotation in the normal rotation direction and one-third rotation in the reverse rotation direction.

In the fourth driving, different driving is performed in accordance with whether cutting tool 5 has been driven in the normal rotation direction or cutting tool 5 has been driven in the reverse rotation direction in the third driving. First, when cutting tool 5 has been driven in the normal rotation direction in the third driving, the fourth driving has two types of drivings in accordance with a result of comparison between detected load t and reference load s by comparing circuit 110, similarly to the second driving. Specifically, if detected load t is smaller than reference load s (t<s), controller 11 executes control to perform the driving for further rotating cutting tool 5 in the normal rotation direction by 180 degrees (corresponding to step S81 shown in FIG. 9). As a result, controller 11 has executed control to perform the driving such that cutting tool 5 makes one-half rotation in the normal rotation direction and one-sixth rotation in the reverse rotation direction, and thereafter, one rotation in the normal rotation direction. On the other hand, if detected load t is equal to or larger than reference load s (t≥s), controller 11 executes control to perform the driving for rotating cutting tool 5 in the reverse rotation direction by 60 degrees (corresponding to step S84 shown in FIG. 9). As a result, controller 11 has executed control to perform twice the driving for causing cutting tool 5 to make one-half rotation in the normal rotation direction and one-sixth rotation in the reverse rotation direction.

When cutting tool 5 has been driven in the reverse rotation direction in the third driving, the fourth driving has two types of drivings in accordance with a result of comparison between detected load t and reference load s by comparing circuit 110, similarly to the second driving. Specifically, if detected load t is smaller than reference load s (t<s), controller 11 executes control to perform the driving for rotating cutting tool 5 in the normal rotation direction by 180 degrees (corresponding to step S81 shown in FIG. 9). As a result, controller 11 has executed control to perform the driving such that cutting tool 5 makes one-half rotation in the normal rotation direction and one-third rotation in the reverse rotation direction, and thereafter, one-half rotation in the normal rotation direction. On the other hand, if detected load t is equal to or larger than reference load s (t≥s), controller 11 executes control to perform the driving for further rotating cutting tool 5 in the reverse rotation direction by 60 degrees (corresponding to step S84 shown in FIG. 9). As a result, controller 11 has executed control to perform the driving such that cutting tool 5 makes one-half rotation in the normal rotation direction and one-half rotation in the reverse rotation direction. In the fifth and subsequent drivings, the drivings described in the first to fourth drivings are repeated, and thus, description will not be repeated.

Figure 11:
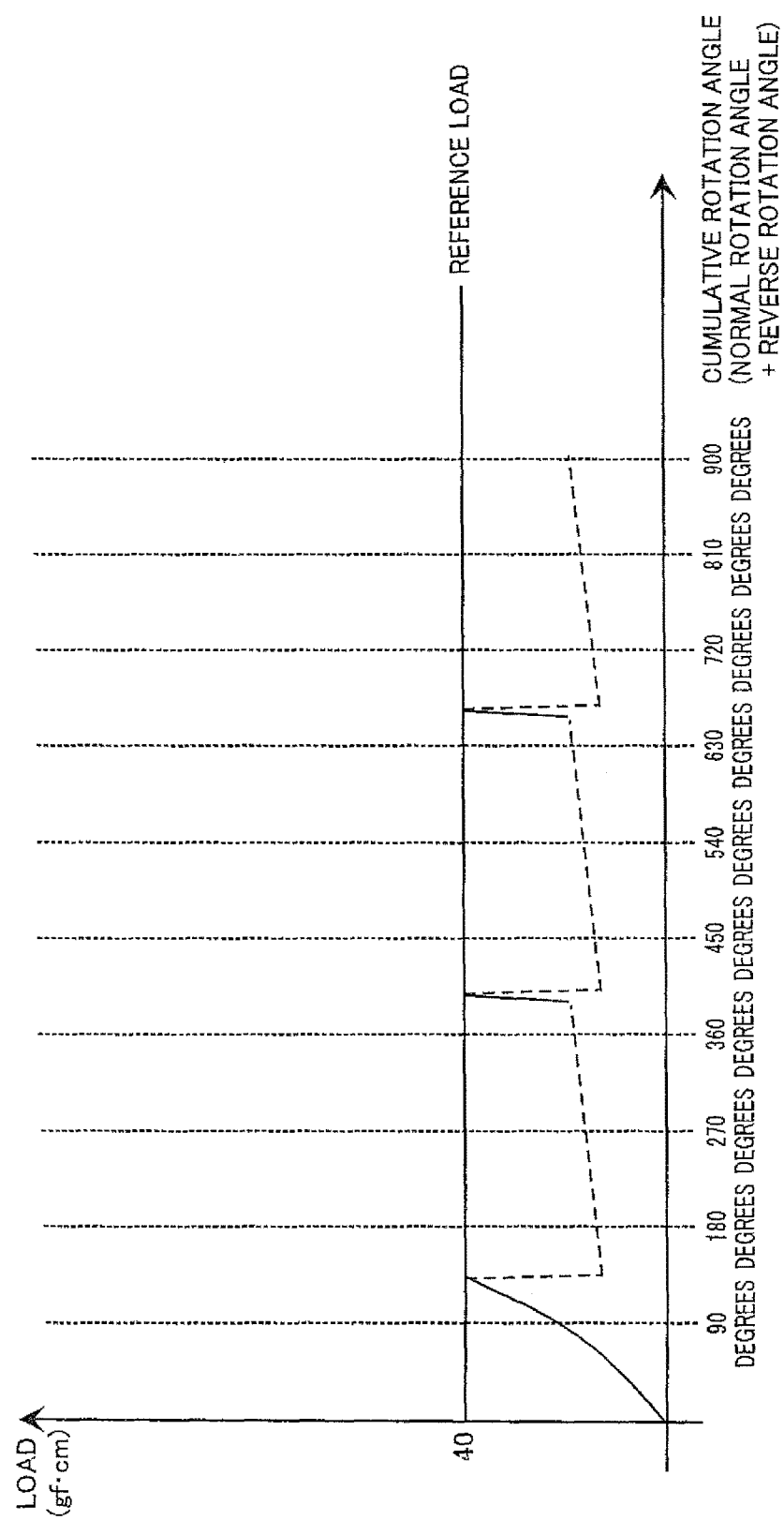
FIG. 11 is a graph showing a change of a load applied to a cutting tool with respect to a cumulative rotation angle of a root canal treating device having an auto torque reverse function.
Figure 12:
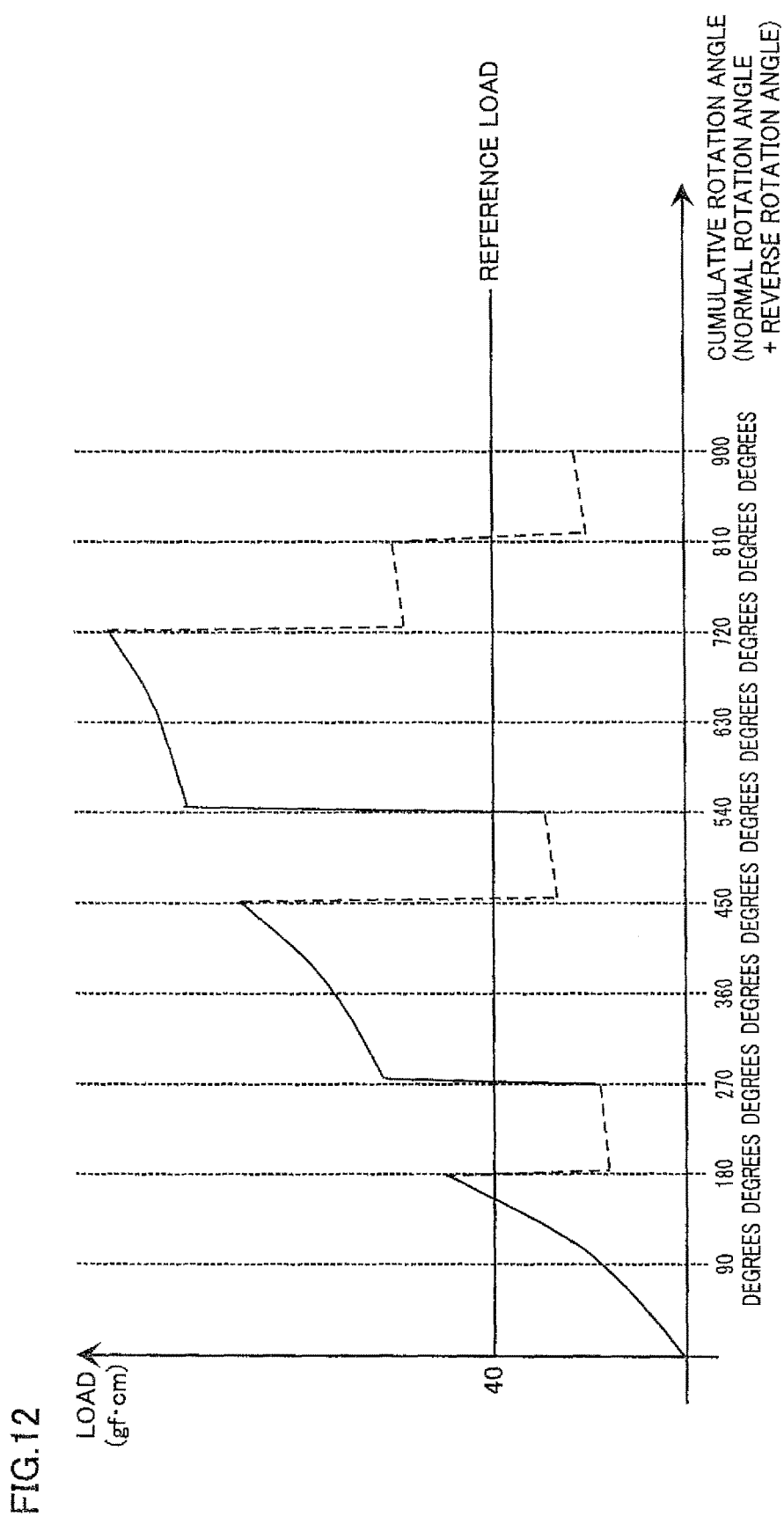
FIG. 12 is a graph showing a change of a load applied to the cutting tool with respect to a cumulative rotation angle of the root canal treating device according to the second embodiment of the present invention.
Figure 13:
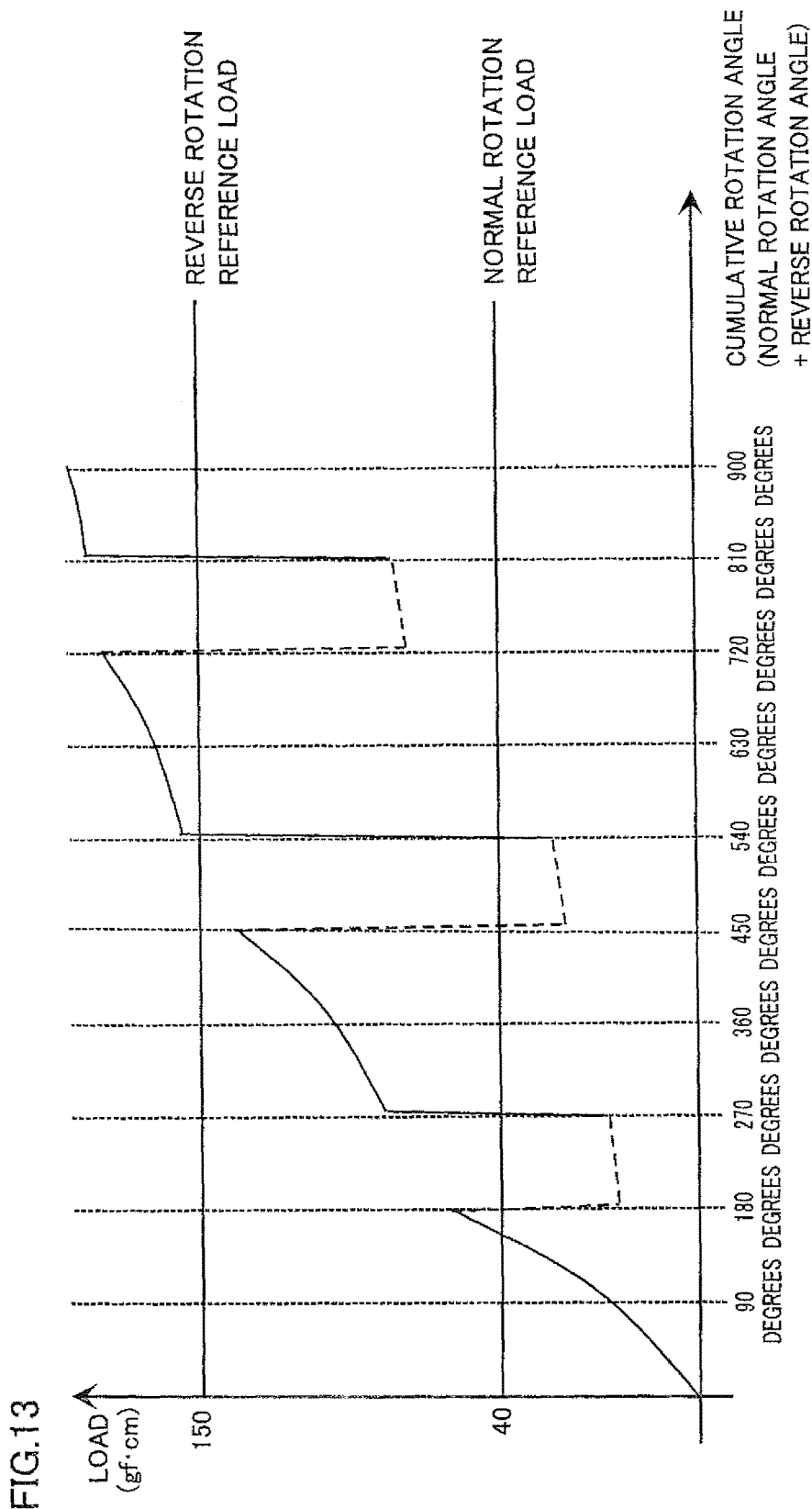
FIG. 13 is a graph showing a change of a load applied to a cutting tool with respect to a cumulative rotation angle of a root canal treating device according to a modification of the second embodiment of the present invention.

Next, a change of the load applied to cutting tool 5 with respect to a cumulative rotation angle will be described. FIG. 11 is a graph showing a change of a load applied to a cutting tool with respect to a cumulative rotation angle of a root canal treating device having an auto torque reverse function. The auto torque reverse function herein refers to a function of rotating the cutting tool in the reverse rotation direction immediately after the detected load reaches a reference (refer to Japanese Patent No. 3264607). On the other hand, FIG. 12 is a graph showing a change of the load applied to cutting tool 5 with respect to a cumulative rotation angle of root canal treating device 100 according to the second embodiment of the present invention. In FIG. 12, the reference load compared with the load detected in the normal rotation direction is the same as the reference load compared with the load detected in the reverse rotation direction. FIG. 13 is a graph showing a change of a load applied to cutting tool 5 with respect to a cumulative rotation angle of root canal treating device 100 according to a modification of the second embodiment of the present invention. In FIG. 13, the reference load compared with the load detected in the reverse rotation direction is larger than the reference load compared with the load detected in the normal rotation direction.

In each of the graphs shown in FIGS. 11, 12 and 13, the horizontal axis indicates the cumulative rotation angle and the vertical axis indicates the load applied to cutting tool 5. The cumulative rotation angle in the horizontal axis is a sum of the magnitude of the rotation angle in the normal rotation direction (normal rotation angle) and the magnitude of the reverse rotation angle in the reverse rotation direction (reverse rotation angle), and is expressed in the unit of degree. The load applied to cutting tool 5 in the vertical axis is expressed in the unit of gf·cm. In addition, in each of the graphs shown in FIGS. 11, 12 and 13, a change of the load when cutting tool 5 is rotated in the normal rotation direction is indicated by a solid line, and a change of the load when cutting tool 5 is rotated in the reverse rotation direction is indicated by a broken line.

In the root canal treating device having the auto torque reverse function as shown in FIG. 11, the reference load for rotating the cutting tool in the reverse rotation direction is set at 40 gf·cm. In the root canal treating device having the auto torque reverse function, when the load applied to the cutting tool reaches the reference load (40 gf·cm), the cutting tool is rotated in the reverse rotation direction to some extent to reduce the load applied to the cutting tool, and then, the cutting tool is rotated in the normal rotation direction again. In the example shown in FIG. 11, in the root canal treating device, when the cutting tool is rotated in the normal rotation direction until the cumulative rotation angle reaches about 130 degrees from 0 degree, the load applied to the cutting tool reaches the reference load and the cutting tool rotates in the reverse rotation direction. In the root canal treating device, when the cumulative rotation angle is between about 130 degrees and about 390 degrees, the cutting tool is rotated in the reverse rotation direction, and thereafter, when the cumulative rotation angle reaches about 390 degrees, the cutting tool is rotated in the normal rotation direction again. In the root canal treating device, the load applied to the cutting tool reaches the reference load when the cutting tool is rotated in the normal rotation direction by about 10 degrees (the cumulative rotation angle is about 400 degrees), and thus, the cutting tool is rotated in the reverse rotation direction again. Similarly, in the root canal treating device, when the cumulative rotation angle reaches about 660 degrees, the cutting tool is rotated in the normal rotation direction again. However, the load applied to the cutting tool reaches the reference load when the cutting tool is rotated in the normal rotation direction by about 10 degrees (the cumulative rotation angle is about 670 degrees), and thus, the cutting tool is rotated in the reverse rotation direction again.

In the example shown in FIG. 11, in the root canal treating device, the cutting tool is rotated until the cumulative rotation angle reaches 900 degrees. Of 900 degrees, the rotation angle of rotating the cutting tool in the normal rotation direction is 130 degrees+10 degrees+10 degrees=150 degrees. Namely, in the root canal treating device, only about one-sixth of the driving is the rotation in the normal rotation direction that contributes to cutting of the tooth.

On the other hand, also in root canal treating device 100 according to the second embodiment shown in FIG. 12, the reference load is set at 40 gf·cm. However, in root canal treating device 100 according to the second embodiment, controller 11 maintains the rotation direction of cutting tool 5 in the normal rotation direction during the normal rotation period until the driving for rotating cutting tool 5 in the normal rotation direction by motor driver 13 satisfies the predetermined rotation angle (e.g., 180 degrees) or the predetermined rotation time (e.g., 0.25 seconds). Therefore, even when the load applied to cutting tool 5 is equal to or larger than the reference load during the normal rotation period, controller 11 maintains the rotation direction of cutting tool 5 in the normal rotation direction until the predetermined rotation angle or the predetermined rotation time is satisfied. Furthermore, in root canal treating device 100 according to the second embodiment, controller 11 maintains the rotation direction of cutting tool 5 in the reverse rotation direction during the reverse rotation period until the driving for rotating cutting tool 5 in the reverse rotation direction by motor driver 13 satisfies the predetermined reverse rotation angle (e.g., 90 degrees) or the predetermined reverse rotation time (e.g., about 0.13 seconds).

In the example shown in FIG. 12, in root canal treating device 100, when the cumulative rotation angle reaches about 150 degrees, the load applied to cutting tool 5 becomes equal to or larger than the reference load. However, cutting tool 5 is rotated in the normal rotation direction until the cumulative rotation angle reaches 180 degrees, and when the cumulative rotation angle reaches 180 degrees, cutting tool 5 is rotated in the reverse rotation direction. In root canal treating device 100, until the cumulative rotation angle reaches 270 degrees, cutting tool 5 is rotated in the reverse rotation direction such that the load applied to cutting tool 5 becomes smaller than the reference load. Thereafter, in root canal treating device 100, cutting tool 5 is rotated in the normal rotation direction again and the load applied to cutting tool 5 becomes equal to or larger than the reference load again. However, in root canal treating device 100, even when the load applied to cutting tool 5 becomes equal to or larger than the reference load again, cutting tool 5 is rotated in the normal rotation direction until the cumulative rotation angle reaches 450 degrees, and when the cumulative rotation angle reaches 450 degrees, cutting tool 5 is rotated in the reverse rotation direction.

In root canal treating device 100, until the cumulative rotation angle reaches 540 degrees, cutting tool 5 is rotated in the reverse rotation direction such that the load applied to cutting tool 5 becomes smaller than the reference load. Thereafter, in root canal treating device 100, cutting tool 5 is rotated in the normal rotation direction again and the load applied to cutting tool 5 becomes equal to or larger than the reference load again. However, in root canal treating device 100, even when the load applied to cutting tool 5 becomes equal to or larger than the reference load again, cutting tool 5 is rotated in the normal rotation direction until the cumulative rotation angle reaches 720 degrees, and when the cumulative rotation angle reaches 720 degrees, cutting tool 5 is rotated in the reverse rotation direction.

Thereafter, in root canal treating device 100, cutting tool 5 is rotated in the reverse rotation direction until the cumulative rotation angle reaches 810 degrees. However, the load applied to cutting tool 5 cannot be reduced to become smaller than the reference load. Therefore, in root canal treating device 100, cutting tool 5 is further rotated in the reverse rotation direction until the cumulative rotation angle reaches 900 degrees. In root canal treating device 100, cutting tool 5 is rotated in the reverse rotation direction until the cumulative rotation angle reaches 900 degrees, and thereby, the load applied to cutting tool 5 is reduced to become smaller than the reference load. In the example shown in FIG. 12, in root canal treating device 100, cutting tool 5 is rotated until the cumulative rotation angle reaches 900 degrees. Of 900 degrees, the rotation angle of rotating cutting tool 5 in the normal rotation direction is 180 degrees+180 degrees+180 degrees=540 degrees. Namely, in root canal treating device 100, as much as about three-fifths of the driving is the rotation in the normal rotation direction that contributes to cutting of the tooth. Therefore, in root canal treating device 100 according to the second embodiment, the tooth cutting efficiency can be enhanced to be about 3.6 times higher than that of the root canal treating device having the auto torque reverse function.

In addition, in the root canal treating device having the auto torque reverse function, it is necessary to set the reference load to be large and prevent the rotation direction from being easily controlled from the normal rotation direction to the reverse rotation direction, in order to obtain the same degree of the tooth cutting efficiency as that of root canal treating device 100 according to the second embodiment. Conversely, in root canal treating device 100 according to the second embodiment, sufficient tooth cutting efficiency can be obtained even when the reference load is set to be small. Namely, in root canal treating device 100 according to the second embodiment, by setting the reference load to be small, a burden on cutting tool 5 can be reduced and sufficient cutting of the tooth becomes possible.

For example, in root canal treating device 100 according to the second embodiment, the reference load can be set at up to 20 gf·cm when cutting tool 5 has a diameter of 0.1 mm. The reference load can be set at up to 40 gf·cm when cutting tool 5 has a diameter of 0.25 mm. The reference load can be set at up to 60 gf·cm when cutting tool 5 has a diameter of 0.4 mm.

Furthermore, in root canal treating device 100 according to the modification of the second embodiment, the reference load compared with the load detected in the reverse rotation direction is set to be larger than the reference load compared with the load detected in the normal rotation direction, and thereby, the tooth cutting efficiency can be further enhanced. In root canal treating device 100 according to the second embodiment shown in FIG. 13, the reference load (normal rotation reference load) compared with the load detected in the normal rotation direction is set at 40 gf·cm, and the reference load (reverse rotation reference load) compared with the load detected in the reverse rotation direction is set at 150 gf·cm.

In the example shown in FIG. 13, in root canal treating device 100, when the cumulative rotation angle reaches about 150 degrees, the load applied to cutting tool 5 becomes equal to or larger than the normal rotation reference load. However, cutting tool 5 is rotated in the normal rotation direction until the cumulative rotation angle reaches 180 degrees, and when the cumulative rotation angle reaches 180 degrees, cutting tool 5 is rotated in the reverse rotation direction. In root canal treating device 100, cutting tool 5 is rotated in the reverse rotation direction until the cumulative rotation angle reaches 270 degrees such that the load applied to cutting tool 5 becomes smaller than the reverse rotation reference load and the normal rotation reference load. Thereafter, in root canal treating device 100, cutting tool 5 is rotated in the normal rotation direction again and the load applied to cutting tool 5 becomes equal to or larger than the normal rotation reference load again. However, in root canal treating device 100, even when the load applied to cutting tool 5 becomes equal to or larger than the reference load again, cutting tool 5 is rotated in the normal rotation direction until the cumulative rotation angle reaches 450 degrees, and when the cumulative rotation angle reaches 450 degrees, cutting tool 5 is rotated in the reverse rotation direction.

In root canal treating device 100, until the cumulative rotation angle reaches 540 degrees, cutting tool 5 is rotated in the reverse rotation direction such that the load applied to cutting tool 5 becomes smaller than the reverse rotation reference load and the normal rotation reference load. Thereafter, in root canal treating device 100, cutting tool 5 is rotated in the normal rotation direction again and the load applied to cutting tool 5 becomes equal to or larger than the normal rotation reference load again. However, in root canal treating device 100, even when the load applied to cutting tool 5 becomes equal to or larger than the normal rotation reference load again, cutting tool 5 is rotated in the normal rotation direction until the cumulative rotation angle reaches 720 degrees, and when the cumulative rotation angle reaches 720 degrees, cutting tool 5 is rotated in the reverse rotation direction.

Thereafter, in root canal treating device 100, cutting tool 5 is rotated in the reverse rotation direction until the cumulative rotation angle reaches 810 degrees. However, the load applied to cutting tool 5 cannot be reduced to become smaller than the normal rotation reference load. However, in root canal treating device 100, the load applied to cutting tool 5 is smaller than the reverse rotation reference load, and thus, cutting tool 5 is not rotated in the reverse rotation direction and cutting tool 5 is further rotated in the normal rotation direction again until the cumulative rotation angle reaches 900 degrees. In the example shown in FIG. 13, in root canal treating device 100, cutting tool 5 is rotated until the cumulative rotation angle reaches 900 degrees. Of 900 degrees, the rotation angle of rotating cutting tool 5 in the normal rotation direction is 180 degrees+180 degrees+180 degrees+90 degrees=630 degrees. Namely, in root canal treating device 100, as much as about seven-tenths of the driving is the rotation in the normal rotation direction that contributes to cutting of the tooth. Therefore, in root canal treating device 100 according to the second embodiment, by setting the reverse rotation reference load to be larger than the normal rotation reference load, the tooth cutting efficiency can be further enhanced.

As described above, in root canal treating device 100 according to the second embodiment, controller 11 maintains the rotation direction of cutting tool 5 in the reverse rotation direction during the reverse rotation period until the driving for rotating cutting tool 5 in the reverse rotation direction by motor driver 13 satisfies the predetermined reverse rotation angle or the predetermined reverse rotation time (corresponding to step S84 shown in FIG. 9). Controller 11 compares the load detected by resistor 13*d* for load detection and the reference load during the reverse rotation period, and when the detected load is equal to or larger than the reference load (corresponding to step S86 shown in FIG. 9), controller 11 further controls the rotation direction of cutting tool 5 to the reverse rotation direction. As a result, controller 11 according to the second embodiment executes control such that motor driver 13 continuously drives cutting tool 5 in the reverse rotation direction, and thereby, the load applied to cutting tool 5 can be further reduced and breakage of cutting tool 5 can be prevented.

(Modification)

In the flowchart shown in FIG. 9, in step S84, controller 11 executes control to maintain the rotation direction of cutting tool 5 in the reverse rotation direction until the driving for rotating cutting tool 5 in the reverse rotation direction by motor driver 13 satisfies the predetermined reverse rotation angle (e.g., 60 degrees) or the predetermined reverse rotation time (e.g., about 0.08 seconds) (during the reverse rotation period). Thereafter, in step S85, comparing circuit 110 compares the detected load and the set reference load. Root canal treating device 100 according to the second embodiment is not, however, limited thereto. Controller 11 does not execute control to maintain the rotation direction of cutting tool 5 in the reverse rotation direction during the reverse rotation period, but may only execute control to perform the driving for continuously rotating cutting tool 5 in the reverse rotation direction during the reverse rotation period. Namely, root canal treating device 100 according to the second embodiment may be configured such that comparing circuit 110 compares the detected load and the set reference load at a timing at which cutting tool 5 rotating continuously in the reverse rotation direction rotates by the predetermined reverse rotation angle or for the predetermined reverse rotation time. It should be noted that the process in steps S81 to S83 is the same as the process in steps S61 to S63 shown in FIG. 6.

Figure 14:
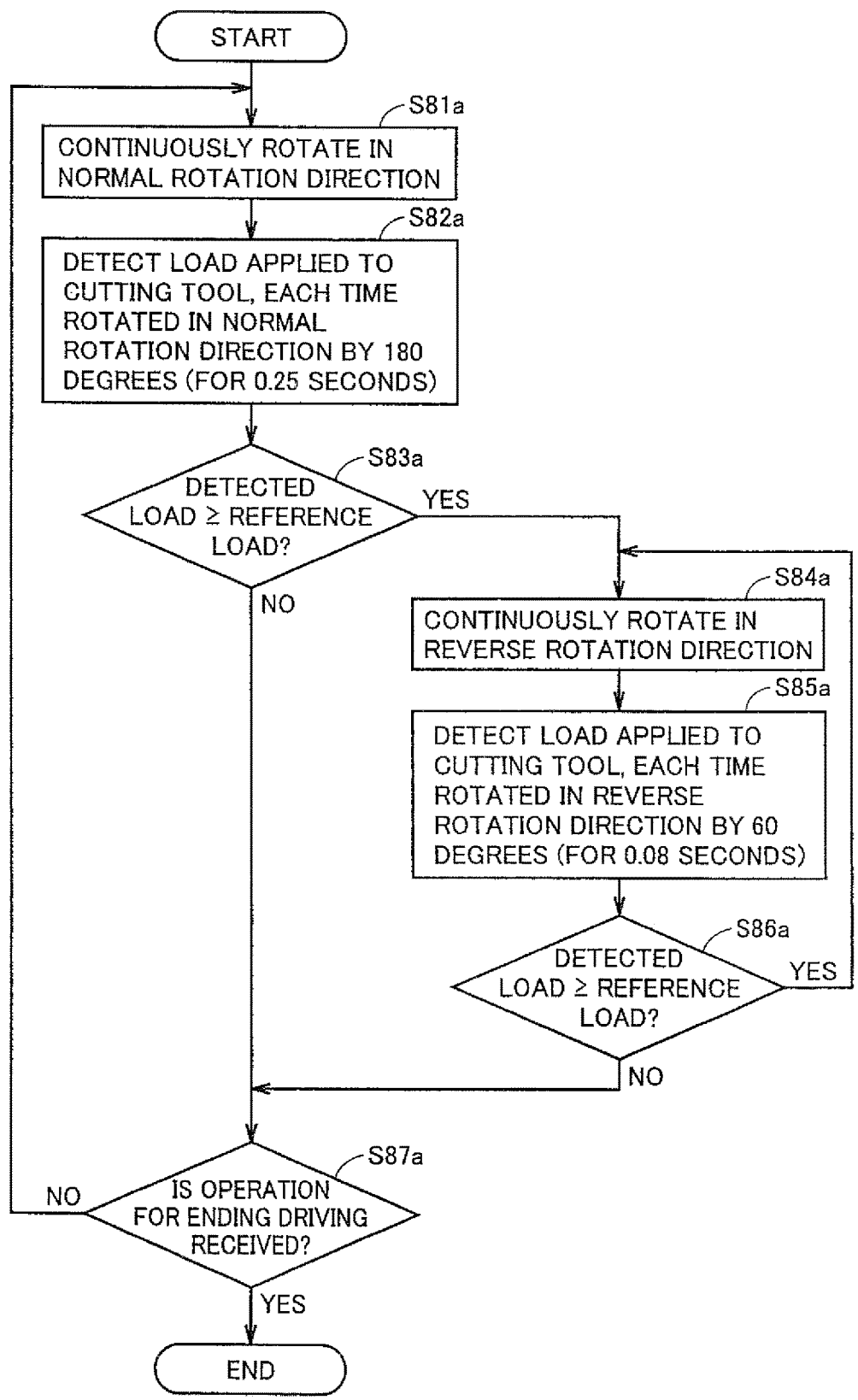
FIG. 14 is a flowchart for describing one example of driving of the cutting tool of the root canal treating device according to the modification of the second embodiment of the present invention.

Specific description will be given to a modification in which control is executed to perform the driving for continuously rotating cutting tool 5 in the reverse rotation direction, instead of the control in step S84. FIG. 14 is a flowchart for describing one example of driving of cutting tool 5 of root canal treating device 100 according to the modification of the second embodiment of the present invention. First, controller 11 executes control to perform the driving for continuously rotating cutting tool 5 in the normal rotation direction by motor driver 13 (step S81*a*). The initial values set in controller 11 are used as the number of normal rotations and the number of reverse rotations, and they are not changed in the process in the flowchart shown in FIG. 14.

Next, by using resistor 13*d* for load detection, controller 11 detects the load applied to cutting tool 5, when cutting tool 5 is rotated in the normal rotation direction by the predetermined rotation angle (e.g., 180 degrees) or for the predetermined rotation time (e.g., 0.25 seconds) (step S82*a*). Resistor 13*d* for load detection may detect the load applied to cutting tool 5 at any point in time during rotation of cutting tool 5 in the normal rotation direction by 180 degrees, or a maximum value or an average value of the detected load or at least one of a plurality of detected load values may be used.

Next, comparing circuit 110 compares the load detected by resistor 13*d* for load detection and the reference load set by variable resistor 14*a* for setting the reference load in setting unit 14, when cutting tool 5 is rotated in the normal rotation direction by the predetermined rotation angle or for the predetermined rotation time (step S83*a*). As a result, it is possible to detect cutting into the root canal wall by cutting tool 5, which is one cause of breakage of cutting tool 5. If the detected load is equal to or larger than the reference load (YES in step S83*a*), controller 11 executes control to perform the driving for continuously rotating cutting tool 5 in the reverse rotation direction by motor driver 13 (step S84*a*).

Next, by using resistor 13*d* for load detection, controller 11 detects the load applied to cutting tool 5, when cutting tool 5 is rotated in the reverse rotation direction by the predetermined reverse rotation angle (e.g., 60 degrees) or for the predetermined reverse rotation time (e.g., about 0.08 seconds) (step S85*a*). Resistor 13*d* for load detection may detect the load applied to cutting tool 5 at any point in time during rotation of cutting tool 5 in the reverse rotation direction by 60 degrees, or a maximum value or an average value of the detected load or at least one of a plurality of detected load values may be used.

Next, comparing circuit 110 compares the load detected by resistor 13*d* for load detection and the reference load set by variable resistor 14*a* for setting the reference load in setting unit 14, when cutting tool 5 is rotated in the reverse rotation direction by the predetermined reverse rotation angle or for the predetermined reverse rotation time (step S85*a*). As a result, it is possible to detect cutting into the root canal wall by cutting tool 5 after cutting tool 5 is rotated in the reverse rotation direction. If the detected load is equal to or larger than the reference load (YES in step S86*a*), controller 11 executes control again to perform the driving for continuously rotating cutting tool 5 in the reverse rotation direction by motor driver 13 (step S84*a*). If the detected load is smaller than the reference load (NO in steps S83*a* and S86*a*), controller 11 determines whether the operation for ending the driving is received from operation unit 15 or not (step S87*a*).

As described above, in root canal treating device 100 according to the modification of the second embodiment, in the case of continuously driving cutting tool 5 in the reverse rotation direction, the load applied to cutting tool 5 and the reference load are compared each time cutting tool 5 is driven in the reverse rotation direction by the predetermined reverse rotation angle or for the predetermined reverse rotation time, and when the load applied to cutting tool 5 is equal to or larger than the reference load, the rotation direction of cutting tool 5 is further controlled to the reverse rotation direction. Therefore, also in root canal treating device 100 according to the modification of the second embodiment, breakage of the cutting tool due to the applied load can be prevented. In addition, the cutting tool can continue to be rotated in the normal rotation direction in accordance with the comparison result, and thus, the tooth cutting efficiency can be enhanced as compared with the twist driving in which cutting tool 5 is rotated in the normal rotation direction and thereafter is rotated in the reverse rotation direction without exception.

(Third Embodiment)

In a root canal treating device according to a third embodiment of the present invention, the parameters such as the reference load, the predetermined rotation angle or the predetermined rotation time in the normal rotation direction, the predetermined reverse rotation angle or the predetermined reverse rotation time, and the number of normal rotations are changed in accordance with a position of the tip end of the cutting tool in the root canal (hereinafter, also simply referred to as "detected position") obtained by the root canal length measuring circuit. In the following description, the case of changing the reference load in accordance with the detected position and the case of changing the predetermined rotation angle or the predetermined rotation time in accordance with the detected position will be described in detail.

The root canal treating device according to the third embodiment has the same configuration as that of root canal treating device 100 according to the first embodiment shown in FIGS. 1 to 3, and thus, the same reference characters are used and detailed description will not be repeated.

First, the reference load set in accordance with the position of cutting tool 5 in root canal treating device 100 according to the third embodiment will be described. In root canal treating device 100 according to the third embodiment, as a distance from the detected position to a reference position (|detected position−reference position|) changes in the order of a distance A, a distance B and a distance C (distance A>distance B>distance C), the magnitude of the reference load set in setting unit 14 changes in the order of a load A, a load B, a load C, and a load D (load A>load B>load C>load D). Namely, as cutting tool 5 comes closer to the reference position (e.g., a position of a root apex), the reference load set in setting unit 14 changes to become smaller. As a result, in root canal treating device 100 according to the third embodiment, breakage of cutting tool 5 due to the load near the reference position can be prevented.

Figure 15:
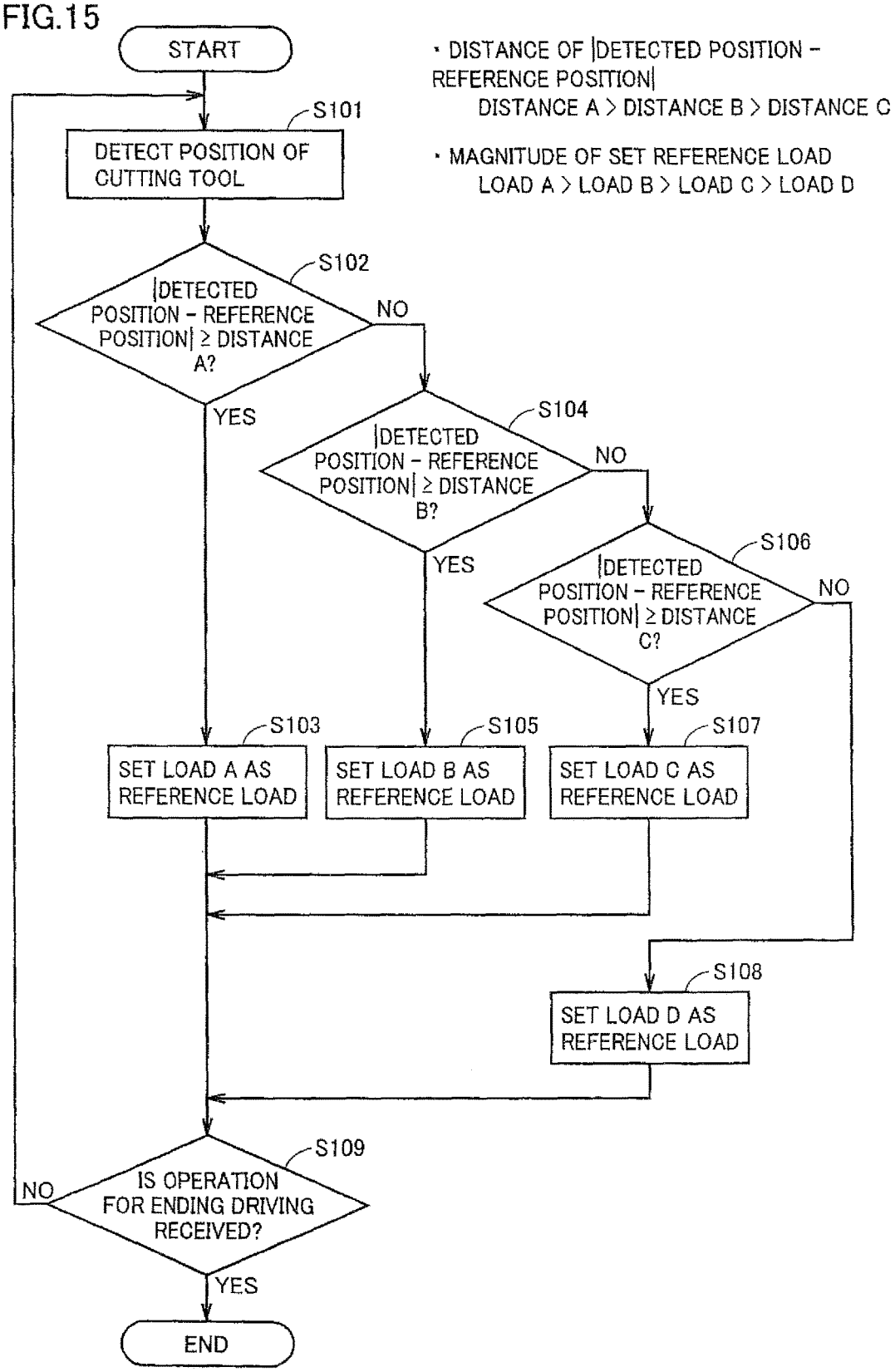
FIG. 15 is a flowchart for describing one example of a reference load set in accordance with a position of a cutting tool in a root canal treating device according to a third embodiment of the present invention.

FIG. 15 is a flowchart for describing one example of the reference load set in accordance with the position of cutting tool 5 in root canal treating device 100 according to the third embodiment of the present invention. First, controller 11 sets the rotation angle in the normal rotation direction (hereinafter, also simply referred to as "normal rotation angle") at 180 degrees and executes control to drive cutting tool 5. Then, controller 11 detects the position of cutting tool 5 obtained by root canal length measuring circuit 12 (step S101).

Next, root canal length measuring circuit 12 determines whether or not the distance from the detected position to the reference position is equal to or longer than distance A (step S102). If root canal length measuring circuit 12 determines that the distance from the detected position to the reference position is equal to or longer than distance A (YES in step S102), controller 11 sets load A as the reference load in setting unit 14 (step S103). If root canal length measuring circuit 12 determines that the distance from the detected position to the reference position is shorter than distance A (NO in step S102), root canal length measuring circuit 12 determines whether or not the distance from the detected position to the reference position is equal to or longer than distance B (step S104).

If root canal length measuring circuit 12 determines that the distance from the detected position to the reference position is equal to or longer than distance B (YES in step S104), controller 11 sets load B as the reference load in setting unit 14 (step S105). If root canal length measuring circuit 12 determines that the distance from the detected position to the reference position is shorter than distance B (NO in step S104), root canal length measuring circuit 12 determines whether or not the distance from the detected position to the reference position is equal to or longer than distance C (step S106).

If root canal length measuring circuit 12 determines that the distance from the detected position to the reference position is equal to or longer than distance C (YES in step S106), controller 11 sets load C as the reference load in setting unit 14 (step S107). If root canal length measuring circuit 12 determines that the distance from the detected position to the reference position is shorter than distance C (NO in step S106), controller 11 sets load D as the reference load in setting unit 14 (step S108).

After any one of loads A to D is set as the reference load in setting unit 14, controller 11 determines whether the operation for ending the driving is received from operation unit 15 or not (step S109). If the operation for ending the driving is received from operation unit 15 (YES in step S109), controller 11 ends the driving. If the operation for ending the driving is not received from operation unit 15 (NO in step S109), the process returns to step S101 and controller 11 detects the position of cutting tool 5 obtained by root canal length measuring circuit 12.

Since the flowchart shown in FIG. 15 is a flowchart for describing setting the reference load, driving of cutting tool 5 is not particularly described. However, in root canal treating device 100 according to the third embodiment, after any one of loads A to D is set as the reference load in setting unit 14, cutting tool 5 is driven in accordance with the driving described in the first and second embodiments.

In addition, the flowchart shown in FIG. 15 describes the example of setting any one of loads A to D as the reference load. The present invention is not, however, limited thereto. The reference load set in setting unit 14 may be changed to become smaller continuously, as cutting tool 5 comes closer to the reference position. Furthermore, the flowchart shown in FIG. 15 describes the example of changing the reference load to become smaller in the order from load A to load D, as cutting tool 5 comes closer to the reference position. The present invention is not, however, limited thereto. As long as the reference load can be changed in accordance with the position detected by root canal length measuring circuit 12, the reference load may be changed in the order of, for example, load A, load C, load B, and load D. In addition, the flowchart shown in FIG. 15 describes the configuration for setting the reference load. The present invention is not, however, limited thereto. The configuration may be replaced with a configuration for setting the reverse rotation reference load or a configuration for setting the reference load and the reverse rotation reference load.

Next, the predetermined rotation angle or the predetermined rotation time set in accordance with the position of cutting tool 5 in root canal treating device 100 according to the third embodiment will be described. In the following description, the example of setting the predetermined rotation angle in accordance with the position of cutting tool 5 will be described. In root canal treating device 100 according to the third embodiment, as the distance from the detected position to the reference position (|detected position−reference position|) changes in the order of distance A, distance B and distance C (distance A>distance B>distance C), the magnitude of the predetermined rotation angle set in setting unit 14 changes in the order of an angle A, an angle B, an angle C, and an angle D (angle A>angle B>angle C>angle D). Namely, as cutting tool 5 comes closer to the reference position (e.g., the position of the root apex), the predetermined rotation angle set in setting unit 14 changes to become smaller. As a result, in root canal treating device 100 according to the third embodiment, breakage of cutting tool 5 due to the load near the reference position can be prevented. In root canal treating device 100 according to the third embodiment, the predetermined reverse rotation angle set in setting unit 14 may be changed to become larger, as cutting tool 5 comes closer to the reference position (e.g., the position of the root apex).

Figure 16:
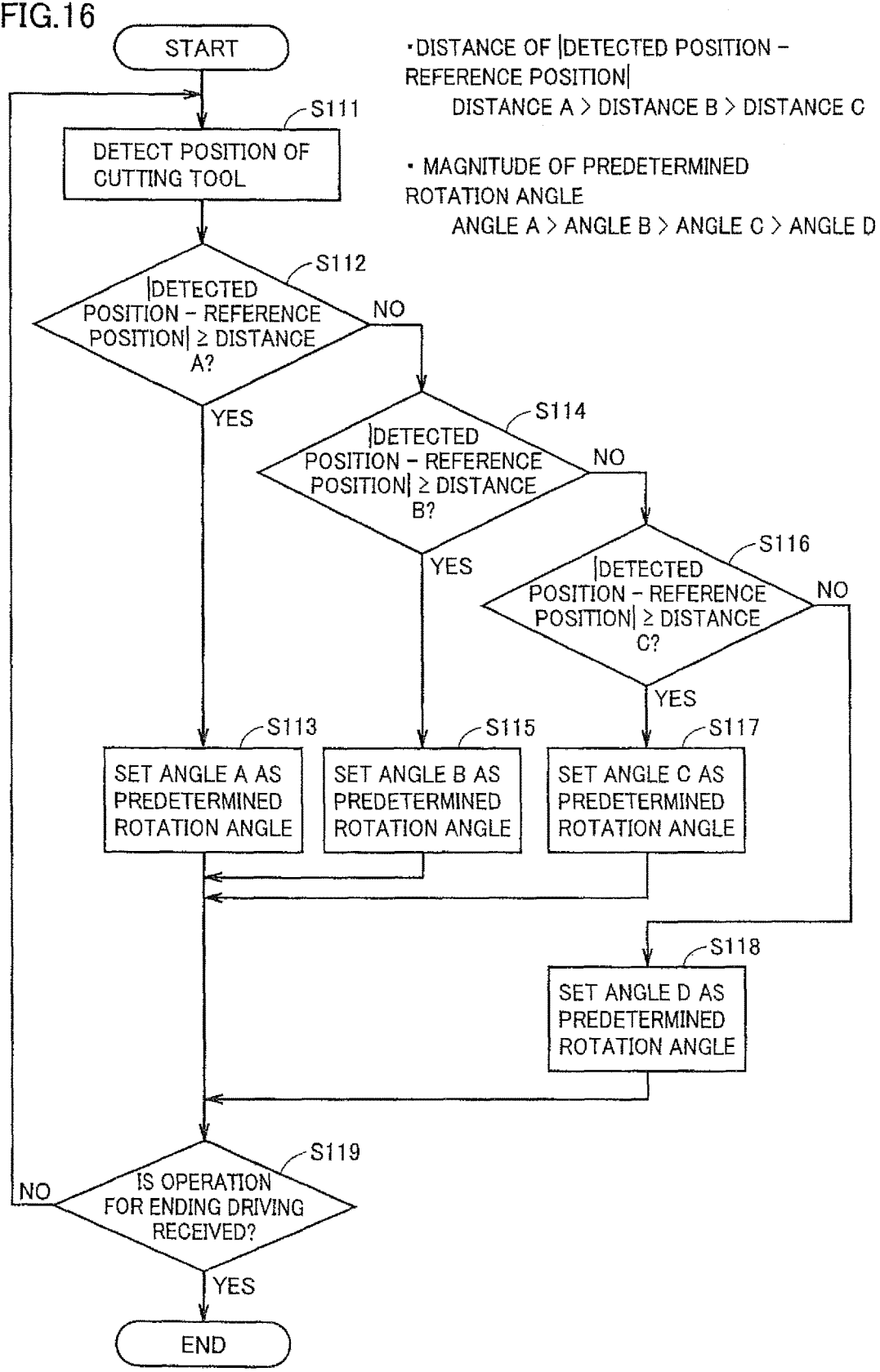
FIG. 16 is a flowchart for describing one example of a predetermined rotation angle set in accordance with the position of the cutting tool in the root canal treating device according to the third embodiment of the present invention.

FIG. 16 is a flowchart for describing one example of the predetermined rotation angle set in accordance with the position of cutting tool 5 in root canal treating device 100 according to the third embodiment of the present invention. First, controller 11 sets the normal rotation angle at 180 degrees and executes control to drive cutting tool 5. Then, controller 11 detects the position of cutting tool 5 obtained by root canal length measuring circuit 12 (step S111).

Next, root canal length measuring circuit 12 determines whether or not the distance from the detected position to the reference position is equal to or longer than distance A (step S112). If root canal length measuring circuit 12 determines that the distance from the detected position to the reference position is equal to or longer than distance A (YES in step S112), controller 11 sets angle A as the predetermined rotation angle in setting unit 14 (step S113). If root canal length measuring circuit 12 determines that the distance from the detected position to the reference position is shorter than distance A (NO in step S112), root canal length measuring circuit 12 determines whether or not the distance from the detected position to the reference position is equal to or longer than distance B (step S114).

If root canal length measuring circuit 12 determines that the distance from the detected position to the reference position is equal to or longer than distance B (YES in step S114), controller 11 sets angle B as the predetermined rotation angle in setting unit 14 (step S115). If root canal length measuring circuit 12 determines that the distance from the detected position to the reference position is shorter than distance B (NO in step S114), root canal length measuring circuit 12 determines whether or not the distance from the detected position to the reference position is equal to or longer than distance C (step S116).

If root canal length measuring circuit 12 determines that the distance from the detected position to the reference position is equal to or longer than distance C (YES in step S116), controller 11 sets angle C as the predetermined rotation angle in setting unit 14 (step S117). If root canal length measuring circuit 12 determines that the distance from the detected position to the reference position is shorter than distance C (NO in step S116), controller 11 sets angle D as the predetermined rotation angle in setting unit 14 (step S118).

After any one of angles A to D is set as the predetermined rotation angle in setting unit 14, controller 11 determines whether the operation for ending the driving is received from operation unit 15 or not (step S119). If the operation for ending the driving is received from operation unit 15 (YES in step S119), controller 11 ends the driving. If the operation for ending the driving is not received from operation unit 15 (NO in step S119), the process returns to step S111 and controller 11 detects the position of cutting tool 5 obtained by root canal length measuring circuit 12.

Since the flowchart shown in FIG. 16 is a flowchart for describing setting the predetermined rotation angle, driving of cutting tool 5 is not particularly described. However, in root canal treating device 100 according to the third embodiment, after any one of angles A to D is set as the predetermined rotation angle in setting unit 14, cutting tool 5 is driven in accordance with the driving described in the first and second embodiments.

In addition, the flowchart shown in FIG. 16 describes the example of setting any one of angles A to D as the predetermined rotation angle. The present invention is not, however, limited thereto. The predetermined rotation angle set in setting unit 14 may be changed to become smaller continuously, as cutting tool 5 comes closer to the reference position. Furthermore, the flowchart shown in FIG. 16 describes the example of changing the predetermined rotation angle to become smaller in the order from angle A to angle D, as cutting tool 5 comes closer to the reference position. The present invention is not, however, limited thereto. As long as the predetermined rotation angle can be changed in accordance with the position detected by root canal length measuring circuit 12, the predetermined rotation angle may be changed in the order of, for example, angle A, angle C, angle B, and angle D. In addition, the flowchart shown in FIG. 16 describes the configuration for setting the predetermined rotation angle. The present invention is not, however, limited thereto. The configuration may be replaced with a configuration for setting the first condition including the predetermined rotation time and the like. Furthermore, the flowchart shown in FIG. 16 describes the configuration for setting the predetermined rotation angle. The present invention is not, however, limited thereto. The configuration may be replaced with a configuration for setting the second condition including the predetermined reverse rotation angle, the predetermined reverse rotation time or the like, or a configuration for setting the first condition and the second condition.

As described above, in root canal treating device 100 according to the third embodiment, as cutting tool 5 comes closer to the reference position, the reference load, the predetermined rotation angle and the like set in setting unit 14 are changed. Therefore, breakage of cutting tool 5 due to the load near the reference position can be prevented. Root canal treating device 100 according to the third embodiment may be configured such that both the reference load and the predetermined rotation angle set in setting unit 14 are changed as cutting tool 5 comes closer to the reference position.

(Fourth Embodiment)

In the description of the configuration of root canal treating device 100 according to the third embodiment, the predetermined rotation angle or the predetermined rotation time set in setting unit 14 is changed as cutting tool 5 comes closer to the reference position. In accordance with a root canal treating device according to a fourth embodiment of the present invention, such a configuration will be described that the predetermined rotation angle or the predetermined rotation time is changed based on the load applied to the cutting tool.

The root canal treating device according to the fourth embodiment has the same configuration as that of root canal treating device 100 according to the first embodiment shown in FIGS. 1 to 3, and thus, the same reference characters are used and detailed description will not be repeated.

Figure 17:
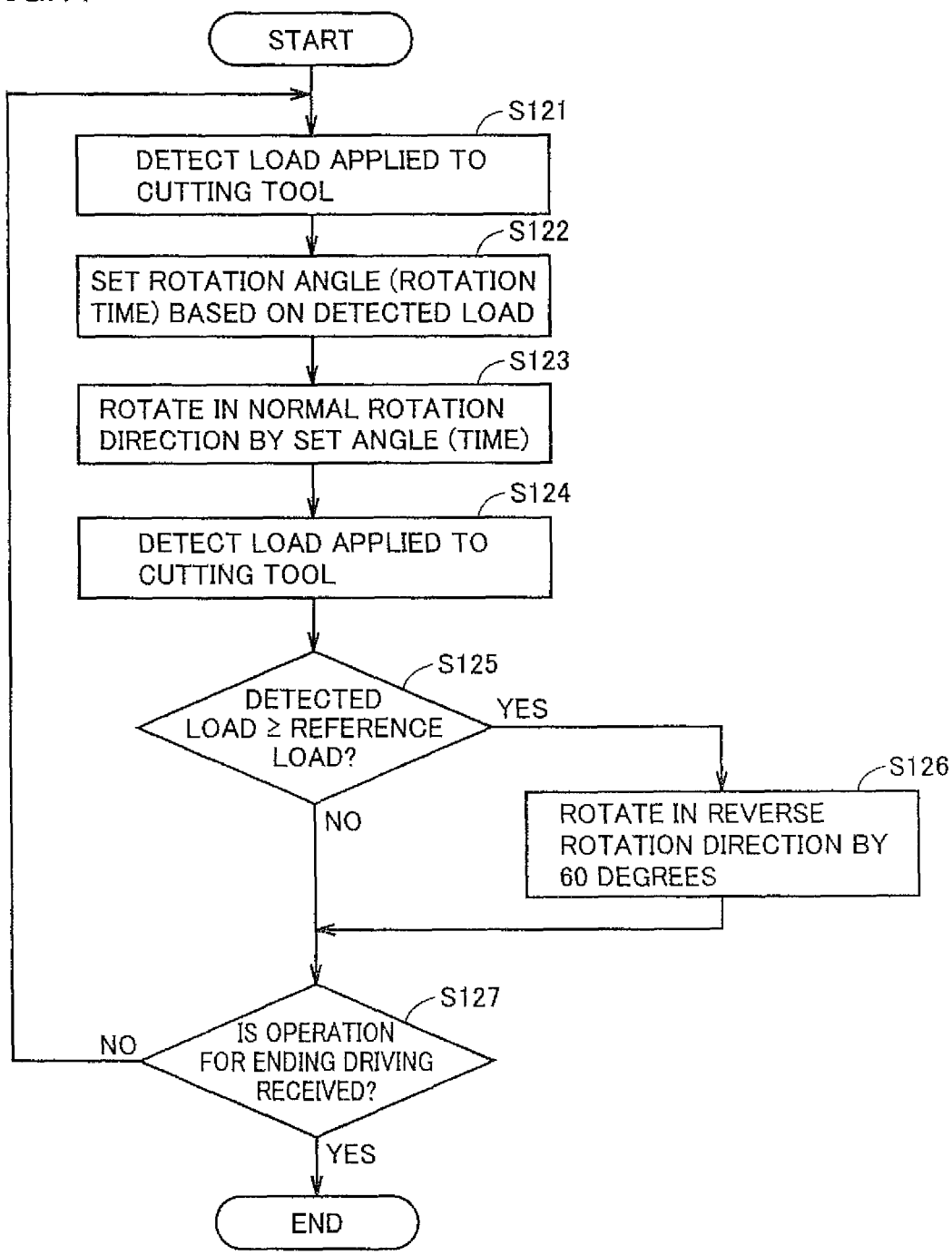
FIG. 17 is a flowchart for describing one example of driving of a cutting tool of a root canal treating device according to a fourth embodiment of the present invention.

FIG. 17 is a flowchart for describing one example of driving of cutting tool 5 of root canal treating device 100 according to the fourth embodiment of the present invention. First, resistor 13d for load detection detects the load applied to cutting tool 5 (step S121). When driving starts, the load applied to cutting tool 5 which is detected by resistor 13d for load detection is "0 (zero)".

Next, controller 11 determines the predetermined rotation angle or the predetermined rotation time based on the load applied to cutting tool 5 which has been detected by resistor 13d for load detection, and sets the determined rotation angle or rotation time in setting unit 14 (step S122). When the load applied to cutting tool 5 which is detected by resistor 13d for load detection is "0 (zero)", controller 11 determines the initial value (e.g., 180 degrees) as the predetermined rotation angle or the predetermined rotation time, and sets the determined rotation angle or rotation time in setting unit 14.

Next, controller 11 executes control to perform the driving for rotating cutting tool 5 in the normal rotation direction by the rotation angle or for the rotation time set in step S121 (step S123). The initial values set in controller 11 are used as the number of normal rotations and the number of reverse rotations, and they are not changed in the process in the flowchart shown in FIG. 17.

Next, by using resistor 13d for load detection, controller 11 detects the load applied to cutting tool 5 when cutting tool 5 is rotated in the normal rotation direction by the rotation angle or for the rotation time set in step S121 (step S124). In the description of the configuration of root canal treating device 100 according to the fourth embodiment, resistor 13d for load detection detects the load applied to cutting tool 5, after cutting tool 5 is rotated in the normal rotation direction by the rotation angle or for the rotation time set in step S121. The present invention is not, however, limited thereto. Resistor 13d for load detection may detect the load applied to cutting tool 5 at any point in time during rotation of cutting tool 5 in the normal rotation direction by the rotation angle or for the rotation time set in step S121. Furthermore, a maximum value or an average value of the load or at least one of a plurality of load values detected by resistor 13d for load detection during rotation by the rotation angle or for the rotation time set in step S121 (during rotation by the predetermined rotation angle or for the predetermined rotation time) may be used as the load applied to cutting tool 5. As a result, appropriate detection of the load applied to cutting tool 5, which is required to prevent breakage of the cutting tool, becomes possible.

Next, comparing circuit 110 compares the load detected by resistor 13d for load detection and the reference load set by variable resistor 14a for setting the reference load in setting unit 14 (step S125). If the detected load is equal to or larger than the reference load (YES in step S125), controller 11 executes control to perform the driving for rotating cutting tool 5 in the reverse rotation direction by 60 degrees (step S126). Namely, controller 11 maintains the rotation direction of cutting tool 5 in the normal rotation direction during the normal rotation period until the driving for rotating cutting tool 5 in the normal rotation direction by motor driver 13 satisfies the predetermined rotation angle or the predetermined rotation time. Controller 11 compares the load detected by resistor 13d for load detection and the reference load during the normal rotation period, and when the detected load is equal to or larger than the reference load, controller 11 controls the rotation direction of cutting tool 5 to the reverse rotation direction. In the description of the configuration of root canal treating device 100 according to the fourth embodiment, the load applied to cutting tool 5 is detected after cutting tool 5 is rotated in the normal rotation direction by the rotation angle or for the rotation time set in step S121, and comparing circuit 110 compares the detected load and the reference load. The present invention is not, however, limited thereto. Root canal treating device 100 according to the fourth embodiment may be configured such that the load applied to cutting tool 5 is detected during rotation by the rotation angle or for the rotation time set in step S121, and comparing circuit 110 compares the detected load and the reference load by the time cutting tool 5 finishes rotating by the rotation angle or for the rotation time set in step S121. As a result, in root canal treating device 100, the next driving can be performed based on the comparison result by comparing circuit 110, immediately after the driving for rotating cutting tool 5 in the normal rotation direction by the rotation angle or for the rotation time set in step S121 is performed. Therefore, cutting tool 5 can be driven efficiently.

Controller 11 also executes control to perform the driving for rotating cutting tool 5 in the normal rotation direction by the rotation angle or for the rotation time set in step S121, and in the reverse rotation direction by 60 degrees. However, in step S121, controller 11 not only determines the predetermined rotation angle or the predetermined rotation time, but also may determine the predetermined reverse rotation angle or the predetermined reverse rotation time and set the determined reverse rotation angle or reverse rotation time in setting unit 14. As a result, in root canal treating device 100, the most appropriate reverse rotation angle or reverse rotation time for driving in the reverse rotation direction can be set.

If the detected load is smaller than the reference load (NO in step S125), or after cutting tool 5 is rotated in the reverse rotation direction by 60 degrees (step S126), controller 11 determines whether the operation for ending the driving is received from operation unit 15 or not (step S127). If the operation for ending the driving is received from operation unit 15 (YES in step S127), controller 11 ends the driving.

If the operation for ending the driving is not received from operation unit 15 (NO in step S127), the process returns to step S121 and resistor 13d for load detection detects the load applied to cutting tool 5.

As described above, in root canal treating device 100 according to the fourth embodiment, the predetermined rotation angle or the predetermined rotation time is determined based on the load applied to cutting tool 5 which is detected by resistor 13d for load detection, and the determined rotation angle or rotation time is set in setting unit 14. Therefore, when the load is small, the predetermined rotation angle or the predetermined rotation time that contributes to cutting of the tooth is increased, and thereby, the efficiency of the work for cutting and enlarging the root canal of the tooth can be improved.

Root canal treating device 100 according to the fourth embodiment can be combined with root canal treating device 100 according to the second embodiment (including the modification) and root canal treating device 100 according to the third embodiment. For example, by combining root canal treating device 100 according to the fourth embodiment with root canal treating device 100 according to the second embodiment, cutting tool 5 can be further rotated in the reverse rotation direction by 60 degrees, when the detected load is equal to or larger than the reference load after cutting tool 5 is rotated in the reverse rotation direction by 60 degrees. By combining root canal treating device 100 according to the fourth embodiment with root canal treating device 100 according to the third embodiment, the predetermined rotation angle or the predetermined rotation time can be changed based on the load applied to cutting tool 5 and the reference load can be changed in accordance with the position detected by root canal length measuring circuit 12.

(Other Modification)

Figure 18:
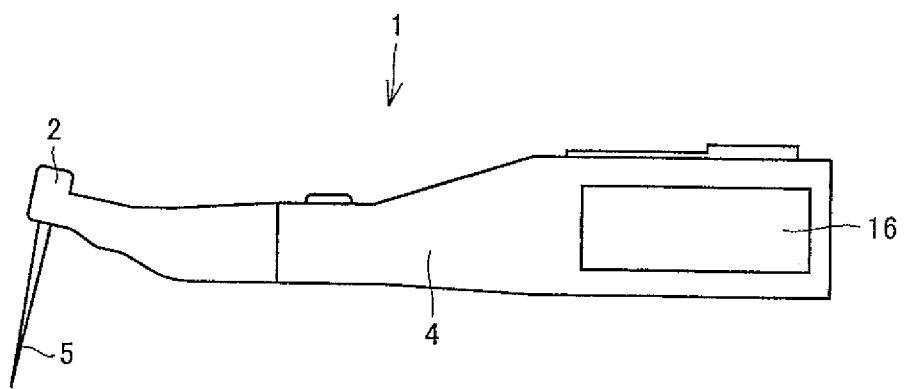
FIG. 18 is a schematic diagram showing a configuration of a cordless-type root canal treating device.

Furthermore, in root canal treating devices 100 according to the first to fourth embodiments, the configuration in which hand piece 1 is coupled to control box 9 via hose 61 has been described. The present invention is not, however, limited thereto but may be configured as a cordless-type root canal treating device. FIG. 18 is a schematic diagram showing a configuration of the cordless-type root canal treating device. In the cordless-type root canal treating device shown in FIG. 18, a battery pack, a micro motor, and a control system corresponding to a control box are incorporated into grip 4 of hand piece 1, and each type of operation units is disposed on a surface of grip 4. Furthermore, in the cordless-type root canal treating device, grip 4 is provided with display unit 16. Therefore, without significantly changing a user's line of sight, the user can check information such as whether cutting tool 5 is being driven in normal rotation driving or in reverse rotation driving, where the current position of cutting tool 5 is, how much load is being applied to cutting tool 5, and what is the number of rotations. Although not shown, lead 19 for mouth electrode 19a may be configured to be led from grip 4.

In addition, in root canal treating devices 100 according to the first to fourth embodiments, the case where micro motor 7 is used as a power source for driving cutting tool 5 has been described. The present invention is not, however, limited thereto. Another driving source such as an air turbine may be used.

Root canal treating device 100 according to the first to fourth embodiments may be configured such that setting unit 14 shown in FIG. 2 can set at least one set value of the first condition, the second condition, the reference load, and the rotation speed (the rotation speed in the normal rotation direction or in the reverse rotation direction). For example, setting unit 14 may be configured to be capable of automatically setting the set values such as the first condition, the second condition, the reference load, and the rotation speed, based on a recipe determined in advance by selecting gender, height and the like of patients. Setting unit 14 may also be configured to be capable of storing, as a recipe, the user's preferred set values such as the first condition, the second condition, the reference load, and the rotation speed in advance, or to be capable of storing, as a recipe, the most appropriate set values such as the first condition, the second condition, the reference load, and the rotation speed for each patient in advance.

Furthermore, root canal treating device 100 according to the first to fourth embodiments may be configured such that setting unit 14 stores, as a recipe, the set values such as the first condition, the second condition, the reference load, and the rotation speed in advance in accordance with the type of cutting tool 5 held on head unit 2, and the user reads the recipe stored based on the type of cutting tool 5 held on head unit 2 from setting unit 14, thereby setting the set values such as the first condition, the second condition, the reference load, and the rotation speed. As a matter of course, setting unit 14 may be configured to set the set values such as the first condition, the second condition, the reference load, and the rotation speed by reading the recipe stored based on a result of detection from a sensor provided at head unit 2 to be capable of identifying the type of cutting tool 5.

As shown in FIG. 13, root canal treating device 100 according to the first to fourth embodiments may be configured such that a set value of the reference load (normal rotation reference load) compared with the load detected by resistor 13*d* for load detection when cutting tool 5 is rotating in the normal rotation direction is different from a set value of the reference load (reverse rotation reference load) compared with the load detected by resistor 13*d* for load detection when cutting tool 5 is rotating in the reverse rotation direction. For example, the normal rotation reference load shown in FIG. 13 is set at 40 gf·cm and the reverse rotation reference load shown in FIG. 13 is set at 150 gf·cm. In addition, in root canal treating device 100 according to the first to fourth embodiments, a value of the reference load (normal rotation reference load) compared with the load detected by resistor 13*d* for load detection when cutting tool 5 is rotating in the normal rotation direction may be set to be equal to or smaller than a value of the reference load (reverse rotation reference load) compared with the load detected by resistor 13*d* for load detection when cutting tool 5 is rotating in the reverse rotation direction. For example, the normal rotation reference load and the reverse rotation reference load shown in FIG. 12 are set to have the same value, and a value of the normal rotation reference load shown in FIG. 13 is set to be smaller than a value of the reverse rotation reference load shown in FIG. 13.

In root canal treating device 100 according to the first to fourth embodiments, until the load detected by resistor 13*d* for load detection becomes equal to or larger than the reference load, the rotation angle or the rotation time may be sequentially reduced from the predetermined rotation angle or the predetermined rotation time, each time the detected load and the reference load are compared. Then, in root canal treating device 100, when the load detected by resistor 13*d* for load detection becomes equal to or larger than the reference load, and cutting tool 5 is rotated in the reverse rotation direction by the predetermined reverse rotation angle or for the predetermined reverse rotation time and thereafter cutting tool 5 is rotated in the normal rotation direction, the rotation angle or the rotation time may be returned to the predetermined rotation angle or the predetermined rotation time. For example, in root canal treating device 100, assuming that the predetermined rotation angle is 180 degrees, the rotation angle is reduced to 150 degrees in the case where the rotation direction is maintained in the normal rotation direction in the first comparison, and the rotation angle is reduced to 120 degrees in the case where the rotation direction is maintained in the normal rotation direction in the second comparison. Then, in root canal treating device 100, when the rotation direction is switched to the reverse rotation direction in the n-th comparison and then the rotation direction is switched to the normal rotation direction, the rotation angle is returned to the predetermined rotation angle, i.e., 180 degrees. As a result, in root canal treating device 100, the load accumulated in cutting tool 5 can be reduced when cutting tool 5 is continuously rotated in the normal rotation direction.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A dental treating apparatus, comprising:
a hand piece for drivably holding a cutting tool on a head unit;
a driving unit for driving said cutting tool so as to be rotatable in a normal rotation direction in which said cutting tool cuts an object to be cut and in a reverse rotation direction opposite to said normal rotation direction;
a control unit for controlling a rotation direction of said cutting tool;
a load specifying unit for specifying a load applied to said cutting tool; and
a load comparing unit for comparing the load specified by said load specifying unit and a reference load,
wherein during a normal rotation period until a predetermined first condition of driving said cutting tool is satisfied, said control unit maintains the rotation direction of said cutting tool in said normal rotation direction,
wherein when a result of comparison by said load comparing unit attains a predetermined result during said normal rotation period, said control unit controls the rotation direction of said cutting tool to said reverse rotation direction,
wherein when a predetermined second condition is satisfied, said control unit controls the rotation direction of said cutting tool to be switched from said reverse rotation direction to said normal rotation direction, and
wherein the predetermined second condition is a predetermined reverse rotation angle or a predetermined reverse rotation time.

2. The dental treating apparatus according to claim 1, wherein during driving in said normal rotation direction by said driving unit until said predetermined first condition is satisfied, said load comparing unit compares the load specified by said load specifying unit and said reference load.

3. The dental treating apparatus according to claim 2, wherein during driving in said normal rotation direction by said driving unit until said predetermined first condition is satisfied, said load comparing unit compares the load specified by said load specifying unit and said reference load based on a maximum value, an average value or at least one of a plurality of specified values of the load applied to said cutting tool.

4. The dental treating apparatus according to claim 1, wherein said predetermined result is a case in which the load specified by said load specifying unit becomes equal to or larger than said reference load.

5. The dental treating apparatus according to claim 1, wherein when driving of said cutting tool controlled to said normal rotation direction by said control unit satisfies said predetermined first condition, said load comparing unit compares the load specified by said load specifying unit and said reference load again.

6. The dental treating apparatus according to claim 1, wherein when driving for rotating said cutting tool in said reverse rotation direction by said driving unit satisfies a predetermined second condition, said load comparing unit compares the load specified by said load specifying unit and said reference load, and when the load specified by said load specifying unit is equal to or larger than said reference load as a result of comparison by said load comparing unit, said control unit further controls the rotation direction of said cutting tool to said reverse rotation direction.

7. The dental treating apparatus according to claim 1, wherein said driving unit sets a reverse rotation angular speed when said cutting tool is driven in said reverse rotation direction to be higher than a rotation angular speed when said cutting tool is driven in said normal rotation direction.

8. The dental treating apparatus according to claim 1, further comprising a driving state detecting unit for detecting a position of a tip end of said cutting tool in a root canal obtained by electrical root canal length measurement, wherein said control unit changes said reference load in accordance with said position detected by said driving state detecting unit.

9. The dental treating apparatus according to claim 8, wherein said control unit changes said reference load to become smaller as said position detected by said driving state detecting unit comes closer to a predetermined reference position.

10. The dental treating apparatus according to claim 1, further comprising a driving state detecting unit for detecting a position of a tip end of said cutting tool in a root canal obtained by electrical root canal length measurement, wherein said control unit changes said predetermined first condition in accordance with said position detected by said driving state detecting unit.

11. The dental treating apparatus according to claim 1, further comprising a driving state detecting unit for detecting a position of a tip end of said cutting tool in a root canal obtained by electrical root canal length measurement, wherein said control unit changes said predetermined second condition in accordance with said position detected by said driving state detecting unit.

12. The dental treating apparatus according to claim 1, further comprising a notifier for notifying a user of the rotation direction of said cutting tool controlled by said control unit.

13. The dental treating apparatus according to claim 12, wherein said notifier is a display unit and is provided at said hand piece.

14. The dental treating apparatus according to claim 1, wherein said predetermined first condition is set based on a rotation angle or a rotation time when said driving unit drives said cutting tool in said normal rotation direction, and defines a timing for switching driving to said reverse rotation direction, and said predetermined second condition is set based on a reverse rotation angle or a reverse rotation time when said driving unit drives said cutting tool in said reverse rotation direction, and defines a timing for switching driving to said reverse rotation direction.

15. The dental treating apparatus according to claim 14, wherein the rotation angle or the rotation time set by said predetermined first condition is set to be larger than the reverse rotation angle or the reverse rotation time set by said predetermined second condition.

16. The dental treating apparatus according to claim 15, wherein the reverse rotation angle or the reverse rotation time set by said predetermined second condition is one-half or larger of the rotation angle or the rotation time set by said predetermined first condition.

17. The dental treating apparatus according to claim 14, further comprising a driving state detecting unit for detecting a position of a tip end of said cutting tool in a root canal obtained by electrical root canal length measurement, wherein said control unit changes the rotation angle or the rotation time set by said predetermined first condition to become smaller as said position detected by said driving state detecting unit comes closer to a predetermined reference position.

18. The dental treating apparatus according to claim 14, further comprising a driving state detecting unit for detecting a position of a tip end of said cutting tool in a root canal obtained by electrical root canal length measurement, wherein said control unit changes the reverse rotation angle or the reverse rotation time set by said predetermined second condition to become larger as said position detected by said driving state detecting unit comes closer to a predetermined reference position.

19. The dental treating apparatus according to claim 1, further comprising a setting unit for setting at least one set value of said predetermined first condition, said reference load and a rotation speed.

20. The dental treating apparatus according to claim 1, further comprising a setting unit for setting at least one set value of said predetermined first condition, said reference load and a rotation speed in accordance with a type of said cutting tool held on said head unit.

21. The dental treating apparatus according to claim 19, wherein said reference load can be set at up to 20 gfcm when said cutting tool has a diameter of 0.1 mm, said reference load can be set at up to 40 gfcm when said cutting tool has a diameter of 0.25 mm, and said reference load can be set at up to 60 gfcm when said cutting tool has a diameter of 0.4 mm.

22. The dental treating apparatus according to claim 6, wherein a set value of said reference load compared with the load specified by said load specifying unit when said cutting tool is rotating in said normal rotation direction is different from a set value of said reference load compared with the load specified by said load specifying unit when said cutting tool is rotating in said reverse rotation direction.

23. The dental treating apparatus according to claim 6, wherein a value of said reference load compared with the load specified by said load specifying unit when said cutting tool is rotating in said normal rotation direction is set to be equal to or smaller than a value of said reference load compared with the load specified by said load specifying unit when said cutting tool is rotating in said reverse rotation direction.

24. The dental treating apparatus according to claim 22, further comprising a setting unit for setting at least one set value of said predetermined second condition, said reference load compared with the load specified by said load specifying unit when said cutting tool is rotating in said reverse rotation direction, and a rotation speed in said reverse rotation direction.

25. A dental treating apparatus, comprising:
   a hand piece for drivably holding a cutting tool on a head unit;
   a driving unit for driving said cutting tool so as to be rotatable in a normal rotation direction in which said cutting tool cuts an object to be cut and in a reverse rotation direction opposite to said normal rotation direction;
   a control unit for controlling a rotation direction of said cutting tool;
   a load specifying unit for specifying a load applied to said cutting tool;
   a rotation setting unit for setting a first condition for driving said cutting tool in said normal rotation direction and rotating said cutting tool in said normal rotation direction based on the load specified by said load specifying unit; and
   a load comparing unit for comparing the load specified by said load specifying unit and a reference load,
   wherein during a normal rotation period until said first condition for driving said cutting tool is satisfied, said control unit maintains the rotation direction of said cutting tool in said normal rotation direction,
   wherein when a result of comparison by said load comparing unit attains a predetermined result during said normal rotation period, said control unit controls the rotation direction of said cutting tool to said reverse rotation direction,
   wherein when a predetermined second condition is satisfied, said control unit controls the rotation direction of said cutting tool to be switched from said reverse rotation direction to said normal rotation direction, and
   wherein the predetermined second condition is a predetermined reverse rotation angle or a predetermined reverse rotation time.

26. A driving method for a dental treating apparatus to drive a cutting tool held on a head unit of a hand piece, the driving method comprising:
   a normal rotation driving step of, on the premise that said cutting tool is rotatable in a normal rotation direction in which said cutting tool cuts an object to be cut and in a reverse rotation direction opposite to said normal rotation direction, continuing driving of said cutting tool in said normal rotation direction until a predetermined first condition of driving said cutting tool is satisfied;
   a load comparing step of comparing a load applied to said cutting tool and a reference load after said normal rotation driving step is performed;
   a reverse rotation driving step of driving said cutting tool in said reverse rotation direction when a result of comparison in said load comparing step attains a predetermined result,
   wherein after driving of said cutting tool in said reverse rotation direction is continued until said reverse rotation driving step satisfies a predetermined second condition, said normal rotation driving step drives said cutting tool in said normal rotation direction again, and
   wherein the predetermined second condition is a predetermined reverse rotation angle or a predetermined reverse rotation time.

* * * * *